(12) United States Patent
Song et al.

(10) Patent No.: US 6,750,057 B2
(45) Date of Patent: Jun. 15, 2004

(54) UBIQUITIN LIGASE

(75) Inventors: Wen-Yuan Song, Gainesville, FL (US); Li-Ya Pi, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/896,720

(22) Filed: Jun. 29, 2001

(65) Prior Publication Data

US 2002/0022258 A1 Feb. 21, 2002

Related U.S. Application Data

(60) Provisional application No. 60/215,049, filed on Jun. 29, 2000.

(51) Int. Cl.$^7$ .......................... C12N 15/29; C12N 15/82
(52) U.S. Cl. .................... 435/419; 536/23.2; 536/23.6; 435/468; 435/320.1; 800/278
(58) Field of Search .............................. 536/23.1, 23.2, 536/23.6; 435/320.1, 468, 419; 800/279, 301

(56) References Cited

U.S. PATENT DOCUMENTS 5,952,485 A   9/1999   Ronald et al. ............. 536/23.6

OTHER PUBLICATIONS

Tyers et al 1999, Science 284:601–604.*
Song et al 1995, Science 270:1804–1806.*
Yang et al., "Ubiquitin Protein Ligase Activity of IAPs and Their Degradation in Proteasomes in Response to Apoptotic Stimuli," Science, 288: 874, 2000.
Joazeiro et al., "The Tyrosine Kinase Negative Regulator c–Cbl as a RING–Type, E2 Dependent Ubiquitin–Protein Ligase," Science, 286: 309, 1999.
Song et al., "A Receptor Kinase–Like Protein Encoded by the Rice Disease Resistance Gene, Xa21," Science, 270:1804, 1995.
Dietrich et al., "A Novel Zinc Finger Protein is Encoded by the Arabidopsis LSD1 Gene and Functions as a Negative Regulator Plant Cell Death," Cell, 88: 685, 1997.
Zhang et al., "Transgenic elite Indica rice varieties, resistant to *Xanothomonas oryzae*pv. oryzae," Molecular Breeding, 4: 551, 1998.
Boyes et al., "The *Arabidopsis thaliana* RPMI disease resistance gene product is a peripheral plasma membrane protein that is degraded coincident with the hypersensitive response," Plant Biology, 95: 15849, 1998.
Buschges et al., "The Barley Mlo Gene: A Novel Control Element of Plant Pathogen Resistance," Cell, 88: 695, 1997.
Richberg et al., "Dead cells do tell tales," Current Opinion in Plant Biology, 1: 480, 1998.
Knapp et al., "Expression of a gibberillin–induced lucine–rich repeat receptor–like protein kinase in deepwater rice and its interaction with kinase–associated protein phosphatase," Plant Physiology, 120: 559–569,1999.
Tyers, M. and A. Willems "One Ring to Rule a Superfamily of E3 Ubiquitin Ligases," Science, 284: 601, 1999.
Freemont, P., "Ubiquitination: RING for destruction?," Current Biology 10: R84, 2000.
Levkowitz et al., "Ubiquitin Ligase Activity and Tyrosine Phosphorylation Underlie Suppression of Growth Factor Signaling by c–Cbl/Sli–1," Molecular Cell, 4:1029, 1999.
Ronald, P., "Making Rice Disease–Resistant," Scientific American, 100, 1997.
Barinaga, M., "A New Finger on the Protein Destruction Button," Science, 286: 223, 1999.

* cited by examiner

*Primary Examiner*—Amy J. Nelson
*Assistant Examiner*—David H. Kruse
(74) *Attorney, Agent, or Firm*—Akerman Senterfitt

(57) ABSTRACT

Disclosed are purified nucleic acid molecules encoding polypeptides having ubiquitin ligase activity and the ability to bind XA21. Also disclosed are methods of making disease-resistant plants and methods of screening compounds for the ability to enhance a disease-resistant phenotype in plants.

7 Claims, 3 Drawing Sheets

| | |
|---:|---|
| 1 | atgggtcacg gtgtcagctg cgcccgcacc ggcgacgagc acgacttctt ccgggcggcg |
| 61 | cagctcggcg acctcgacgc cctggccgcc ctcctcgccg ccgacccttc cctcgctcgc |
| 121 | cgcgccaccc tctacgaccg cctctccgttc ctccacatcg ccgccgccaa tggccgcatc |
| 181 | gaggtgctct ccatgttctt ggatcgcggg gcgccgccgg acgcggtgaa tcggcacaag |
| 241 | cagacgccgc tgatgctcgc ggccatgcac ggcaagatcg actgcgtgct caagctcctc |
| 301 | caggccgacg caaatatctt gatgttcgac tcggtgcacg cgaggacctg cctccaccac |
| 361 | gcggcgtact acggccacgt cgactgcctg caggccatcc tcgccgccgc gcagccacg |
| 421 | ccggtggccg actcatgggg tttcgcccgg ttcgtcaacg tcagggacga ccacggcgcc |
| 481 | actccgctgc atctcgcggc caggcagggg cggccggggt gcgtgcaggt gttgctggag |
| 541 | aacggcgcca ttgtgtcggc tttgacagga tcatatggct tccctggaag cacgtcgctt |
| 601 | catttggctg ctcgtagcgg gaacttggat tgcatcagga agctgcttgc ctggggagct |
| 661 | gatcggctcc aaagggattc ggctgggaga attccctatt ctgttgcgct gaaacggaac |
| 721 | catggagcat gtgcagcttt gctgaaccct acatcagcag agcccatggt gtggccatcc |
| 781 | ccacttaagt tcatcagtga gcttgaacca gaagctaagg ctctcctgga agcagctctg |
| 841 | atggaagcca acagggagag ggagaagaaa atcctgaatg gcacaaagta ctccctgcca |
| 901 | tccccttcgc ccggtgatga cagtgccgat gacgatgcat gctcagaggt gagcgacacg |
| 961 | gagctttgct gcatctgctt cgaccaggct tgcaccattg aggtgcaaga ctgtggacat |
| 1021 | caaatgtgtg caccgtgcac gctggcactg tgctgtcaca acaaacccaa tccgacgacc |
| 1081 | ctgacaccgc cctcaccggc ctgcccattc tgccggggca gcatctcacg gctggtggtg |
| 1141 | gcccaaacaa ggtctgcttg tgatcctgac aagccgtcat ccctgcagct caccgggaag |
| 1201 | cggtcgcgtc gatctcacaa cctcagtgag ggcagcagca gcttcaaagg gctaccttcg |
| 1261 | gccatgggct ccttctcaaa gcttggccgt ggctcgagcc gcatggcgga cagtgacagc |
| 1321 | agcaacctgg acaagcctga gcacgatcta tga |

*FIG. 1A*

| | | |
|---|---|---|
| I | MGH<u>GVSCART</u> | 10 |

| | | |
|---|---|---|
| II | GDEHDFFRAAHLGDLDALAALLAADPSLARRATLY | 45 |
| | DRLSVLHIAAANGRIEVLSMFLDRGAPPDAVNR | 78 |
| | HKQTPLMLAAMHGKIDCVLKLLQADANILMFDSV | 112 |
| | HARTCLHHAAYYGHVDCLQAILAAAQTTPVADSWGFARFVNVRDD | 157 |
| | HGATPLHLAARQGRPGCVQVLLENGAIVSALTGSYGF | 194 |
| | PGSTSLHLAARSGNLDCIRKLLAWGADRLQRDSAGRIPYSVA | 236 |
| | LKRNHGACAALLNPTSAEPMVWPSPLKFISELE | 269 |
| | PEAKALLEAALMEANREREKKILNGTKYSLPSPSPG | 305 |

| | | |
|---|---|---|
| III | DDSADDDACSEVS | 318 |

| | | |
|---|---|---|
| IV | DTEL*CC*IC*F*DQA*C*TIEVQD*C*G*H*QM*C*AP*C*TLAL*CC*HNKPNPTTLTP | 363 |
| | PSPA*C*PF*C*RGSISRLVVAQTRS | 385 |

| | | |
|---|---|---|
| V | ACDPDKPSSLQLTRKRSRRSHNLSEGSSSFKGLPSAMGSFSKLGR | 430 |
| | GSSRMADSDSSNLDKPEHDL | 450 |

*FIG. 1B*

| | |
|---|---|
| XB3 | CCICFDQACTIEVQDCGHQM-CAPCTLALCCHNKPNPTTLTPPSPACPFCR |
| c-Cbl | CKICAENDKDVKIEPCGHLM-CTSCLTSWQESEGQG----------------CPFCR |
| IAP | CKICYVEECIVCFVPCGHVVACAKCALSV-----------------DKCPFCR |

*FIG. 1C*

UBIQUITIN LIGASE

CROSS REFERENCE TO RELATED APPLICATION

The present application claims the priority of U.S. provisional patent application No. 60/215,049 filed Jun. 29, 2000.

STATEMENT AS TO FEDERALLY SPONSORED RESEARCH

The invention was made with U.S. government support under grant number NSF NCB-0080155 awarded by the National Science Foundation. The U.S. government may have certain rights in the invention.

FIELD OF THE INVENTION

The invention relates generally to the fields of molecular biology, biochemistry, plant pathology, and agriculture. More particularly, the invention relates to proteins and polynucleotides associated with resistance to microbial plant pathogens.

BACKGROUND

Disease resistance in plants is often controlled by host recognition of specific pathogen determinants. Resistance (R) gene products in a host plant are believed to function as receptors that recognize effector proteins produced directly or indirectly by a pathogen's avirulence genes. Over the past decade, a number of dominant R genes have been characterized from diverse plants. The proteins encoded by these genes can be grouped into several classes based on structure: serine/threonine kinases, proteins with a nucleotide binding site and leucine-rich repeats (NBS-LRR), presumed extracellular LRR-containing proteins with or without a transmembrane domain, and serine/threonine receptor-like kinases. Baker et al., Science 276, 726 (1997); Staskawicz et al., Science 268, 661 (1995); and Wang et al., Plant Cell 10, 765 (1998). Based on their structures, such proteins are thought to mediate their function by modulating intracellular signaling pathways.

The action of R genes is usually associated with a number of defense responses. One such response common in many different plant types is the hypersensitive response (HR). HR is characterized by rapid cell death at the site of the infection that can often be visualized as a dry brown lesion. While the intracellular signaling events that mediate resistance and HR are not completely characterized, it has been hypothesized that recognition of a pathogen-produced effector protein induces a negative regulatory pathway that can degrade the R protein. Such a pathway would regulate the intensity and duration of cell death and other elicited intracellular signals that contribute to the resistance response. Boyes et al., Proc. Natl. Acad. Sci. U.S.A. 95, 15849 (1998); S. G. Moller and N.-H. Chua, J. Mol. Biol. 293, 219 (1999).

One possible molecular mechanism for the negative regulatory pathway is ubiquitin-mediated protein degradation, which plays an important role in controlling the abundance of numerous short-lived proteins. A. Hershko and A. Ciechanover, Annu. Rev. Biochem. 67, 425 (1998); A. Ciechanover, EMBO J. 17, 7151 (1998). In this process, ubiquitin is activated by the ubiquitin-activating enzyme E1, transferred to the ubiquitin-conjugating enzyme E2, and finally linked to a target substrate by the ubiquitin ligase E3. Id. Upon attachment by ubiquitin, the target protein is subjected to degradation by the 26S proteasome. The specificity of the degradation pathway is determined by E3, which binds to the targeted substrate. Characterization of a number of E3s in animal systems indicates that a zinc-binding domain, RING (for Really Interesting New Gene) finger, is essential for many ubiquitin-mediated protein degradation processes. P. S. Freemont, Curr. Biol. 10, R84 (2000); R. J. Deshaies, Annu. Rev. Cell Dev. Biol. 15, 435 (1999).

A model for studying R-mediated plant pathogen resistance is that of rice (*Oryza sativa*) and the bacterial pathogen *Xanthomonas oryzae*, pv. *oryzae* (Xoo). In this system, the rice R gene Xa21 confers resistance to bacterial blight disease caused by Xoo. Transgenic cell lines expressing the protein encoded by Xa21, i.e. XA21, respond with cell death after inoculation with an avirulent strain of Xoo such as Philippine race 6 (strain pXO99 AZ), but not with virulent strain of Xoo such as Korean race 1 (strain DY890931). He et al., Science 288:2360 (2000). Although XA21 is known to be a receptor-like kinase with serine/threonine specificity [U.S. Pat. No. 5,952,485; and Song et al., Science 270, 661 (1995)], the mechanisms by which it mediates resistance and cell death are not completely understood. Identification of molecules that interact with and/or modify XA21 should help clarify these mechanisms, and provide new tools for engineering broad-spectrum, durable disease resistance in rice and other crop plants.

SUMMARY

The invention relates to the discovery of Xb3, a polynucleotide encoding XB3 (for XA21 Binding Protein 3), a protein that interacts with the XA21 kinase. Xb3 was identified in a yeast two-hybrid assay in which a rice cDNA library was screened using the XA21 kinase as bait. The cloned Xb3 was subsequently sequenced. Based on the nucleotide sequence, it was determined that Xb3 encodes a 450 amino acid protein (i.e., XB3) that has a myristoylation site, 8 imperfect copies of ankyrin repeats, and a RING finger motif. Functional studies indicated that XB3 is a substrate for the XA21 serine/threonine kinase, and binds XA21 via its ankyrin repeat domain. Other studies indicated that XB3's RING finger domain ubiquitinates itself, and is required for ubiquitination of XA21. In vivo protein assays indicated that XA21 is rapidly degraded in response to infection with an avirulent strain of Xoo, but not with a virulent strain. Taken together, these results suggest that XB3 serve as an E3 that negatively regulates pathogen resistance and cell death through ubiquitin-mediated protein degradation of XA21.

Accordingly, the invention features a purified nucleic acid that includes a nucleotide sequence which encodes a naturally occurring protein that: (a) shares at least 80% sequence identity with SEQ ID NO:2 and (b) has at least one functional activity of native XB3. For example, nucleic acids having a nucleotide sequence whose complement hybridizes under high stringency conditions to the nucleotide sequence of SEQ ID NO:1; those encoding a protein having the amino acid sequence of SEQ ID NO:2; and those encoding a protein that specifically binds to XA21 are featured in the invention.

In another aspect, the invention features a vector including a nucleic acid of the invention. The vector can have a nucleic acid operably linked to one or more expression control sequences. Also within the invention is a cell containing a nucleic acid of the invention.

Proteins that include an amino acid sequence that shares at least 80% sequence identity with SEQ ID NO:2 and have at least one functional activity of native XB3 (e.g., purified protein whose amino acid sequence is SEQ ID NO:2) are included in the invention. Also featured are purified proteins containing one or more of amino acid residues 1–10, 11–305, and/or 319–385 of SEQ ID NO:2; as well as fusion proteins containing one of the foregoing proteins fused to a heterologous polypeptide.

Within the invention is a purified antibody that specifically binds to a protein of the invention. Such antibody can include a detectable label.

In still another aspect, the invention features several methods, including a screening method for identifying a substance that modulates binding of an XB3 protein to XA21. This method includes the steps of: providing a sample containing the XB3 protein; adding to the sample a candidate substance; adding to the sample XA21; and detecting an increase or decrease in binding of the XB3 protein to XA21 in the presence of the candidate substance, compared to the binding of the XB3 protein to XA21 in the absence of the candidate substance, as an indication that the candidate substance modulates binding of XB3 protein to XA21.

Also within the invention is a method of producing an XB3 protein. This method includes the steps of: providing a cell transformed with an isolated nucleic acid comprising a nucleotide sequence that encodes an XB3 protein; culturing the cell under conditions that allow expression of the XB3 protein; and collecting the XB3 protein from the cultured cell.

Another method within the invention is a screening method for identifying a substance that modulates expression of a gene encoding XB3. This method includes the steps of: providing a test cell; contacting the test cell with a candidate substance; and detecting an increase or decrease in the expression level of the gene encoding XB3 in the presence of the candidate substance, compared to the expression level of the gene encoding XB3 in the absence of the candidate substance, as an indication that the candidate substance modulates the level of expression of the gene encoding XB3.

Yet another method within the invention is a method for isolating a substance that binds XB3. This method includes the steps of: providing a sample of an immobilized XB3; contacting a mixture containing the XB3-binding substance with the immobilized XB3; separating unbound components of the mixture from bound components of the mixture; and recovering the XB3-binding substance from the immobilized XB3 protein. In this method, the XB3-binding substance can be XA21.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By the term "gene" is meant a nucleic acid molecule that codes for a particular protein, or in certain cases a functional or structural RNA molecule. For example, the Xb3 gene encodes the XB3 protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "Xb3 gene," "Xb3 polynucleotide," "Xb3 nucleic acid", or simply "Xb3" is meant a native XB3-encoding nucleic acid sequence, e.g., the native rice Xb3 cDNA (SEQ ID NO: 1; FIG. 1A), genomic sequences from which Xb3 cDNA can be transcribed, and/or allelic variants and homologs of the foregoing. The terms encompass double-stranded DNA, single-stranded DNA, and RNA.

As used herein, "protein" or "polypeptide" are used synonymously to mean any peptide-linked chain of amino acids, regardless of length or post-translational modification, e.g., glycosylation or phosphorylation. An "purified" polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

By the terms "XB3 protein" "XB3 polypeptide," or simply "XB3" is meant an expression product of an Xb3 gene such as the protein of SEQ ID NO:2 (FIG. 1B); or a protein that shares at least 65% (but preferably 75, 80, 85, 90, 95, 96, 97, 98, or 99%) amino acid sequence identity with SEQ ID NO:2 and displays a functional activity of XB3. A "functional activity" of a protein is any activity associated with the physiological function of the protein. For example, functional activities of XB3 include ubiquitin ligase activity, the ability to be phosphorylated by XA21, and the ability to specifically bind XA21 in at least one of the in vitro assays described herein.

When referring to a nucleic acid molecule or polypeptide, the term "native" refers to a naturally-occurring (e.g., a "wild-type") nucleic acid or polypeptide. A "homolog" of a rice Xb3 gene is a gene sequence encoding a XB3 polypeptide isolated from a plant other than rice. Similarly, a "homolog" of a native XB3 polypeptide is an expression product of an Xb3 homolog.

A "fragment" of an Xb3 nucleic acid is a portion of an Xb3 nucleic acid that is less than full-length and comprises at least a minimum length capable of hybridizing specifically with a native Xb3 nucleic acid under stringent hybridization conditions. The length of such a fragment is preferably at least 15 nucleotides, more preferably at least 20 nucleotides, and most preferably at least 30 nucleotides of a native Xb3 nucleic acid sequence. A "fragment" of an XB3 polypeptide is a portion of an XB3 polypeptide that is less than full-length (e.g., a polypeptide consisting of 5, 10, 15, 20, 30, 40, 50, 75, 100 or more amino acids of native XB3), and preferably retains at least one functional activity of native XB3.

When referring to hybridization of one nucleic to another, "low stringency conditions" means in 10% formamide, 5×Denhart's solution, 6×SSPE, 0.2% SDS at 42° C., followed by washing in 1×SSPE, 0.2% SDS, at 50° C.;

"moderate stringency conditions" means in 50% formamide, 5×Denhart's solution, 5×SSPE, 0.2% SDS at 42° C., followed by washing in 0.2×SSPE, 0.2% SDS, at 65° C.; and "high stringency conditions" means in 50% formamide, 5×Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute of one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with a another amino acid having similar characteristics. Examples of conservative amino acid substitutions are ser for ala, thr, or cys; lys for arg; gln for asn, his, or lys; his for asn; glu for asp or lys; asn for his or gin; asp for glu; pro for gly; leu for ile, phe, met, or val; val for ile or leu; ile for leu, met, or val; arg for lys; met for phe; tyr for phe or trp; thr for ser; trp for tyr; and phe for tyr.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors."

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." A "transgenic" or "transformed" cell or organism (e.g., a plant) also includes progeny of the cell or organism, including progeny produced from a breeding program employing such a "transgenic" cell or organism as a parent in a cross. For example, a plant transgenic for Xb3 is one in which Xb3 nucleic acid has been introduced.

By the term "XB3-specific antibody" is meant an antibody that binds XB3 (e.g., a protein having the amino acid sequence of SEQ ID NO:2), and displays no substantial binding to other naturally occurring proteins other than those sharing the same antigenic determinants as XB3. The term includes polyclonal and monoclonal antibodies.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ liters/mole for that second molecule.

The term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1A is the nucleotide sequence of an Xb3 cDNA.

FIG. 1B is sequence listing of the predicted amino acid sequence of the gene product encoded by the Xb3 cDNA described in FIG. 1A. The deduced protein domains are indicated as follows: (I) putative myristoylation site (underlined); (II) ankyrin repeats; (III) unknown; (IV) RING finger; and (V) carboxyl-terminal tail. Highly conserved amino acids in the ankyrin domain are shown in bold. The eight conserved cysteine and histidine residues that are important for zinc-chelating in the RING finger are shown in shadow.

FIG. 1C is a sequence alignment of the RING finger domains of XB3, human c-Cbl, and the baculovirus inhibitor of apoptosis (IAP) (GenBank accession numbers: human c-Cbl, P22681; Baculovirus Inibitor of Apoptosis, P41436.).

DETAILED DESCRIPTION

Figure 2:
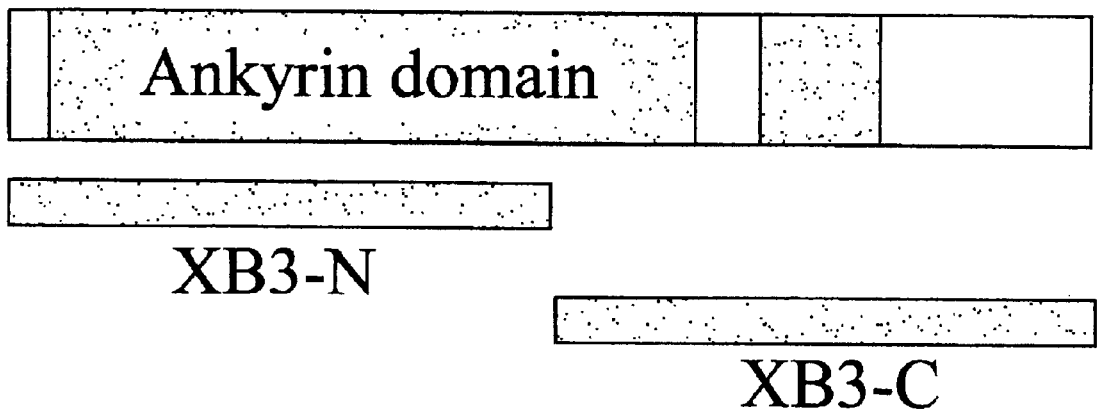
FIG. 2 is a schematic depiction of the structural domains of XB3 and deletion mutants used to test for interactions with the XA21 kinase in yeast two-hybrid assays.

The invention encompasses compositions and methods relating to XB3, an XA21-binding protein. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, ©1991, Whitehead Institute for Biomedical Research, Cambridge, Mass.). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Nucleic Acids Encoding XB3

The invention provides an purified nucleic acid (polynucleotide) that encodes a polypeptide having the amino acid sequence of FIG. 1B (SEQ ID NO:2). The ATCC (American Type Culture Collection) is located at 10801 University Boulevard, Manassas, Va. 20110–2209, USA. A preferred nucleic acid molecule of the invention is the native Xb3 polynucleotide shown in FIG. 1A (SEQ ID NO:1) and deposited with Genbank as Accession No. AF272860. As native Xb3 was discovered in a rice cDNA library, nucleic acid molecules encoding a polypeptide of the present invention can be obtained from rice plants (e.g., *Oryza sativa* spp. Japonica var. Tapei309).

Nucleic acid molecules of the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes native XB3 may be identical to the nucleotide sequence shown in FIG. 1A (SEQ ID NO: 1). It may also be a different coding sequence which, as a result of the redundancy or degeneracy of the genetic code, encodes the same polypeptide as the polynucleotide of SEQ ID NO. 1. Other nucleic acid molecules within the invention are variants of Xb3 such as those that encode fragments, analogs and derivatives of native XB3. Such variants may be, e.g., a naturally occurring allelic variant of native Xb3, a homolog of native Xb3, or a non-naturally occurring variant of native Xb3. These variants have a nucleotide sequence that differs from native Xb3 in one or more bases. For example, the nucleotide sequence of such variants can feature a deletion, addition, or substitution of one or more nucleotides of a native Xb3. Nucleic acid insertions are preferably of about 1 to 10 contiguous nucleotides, and deletions are preferably of about 1 to 30 contiguous nucleotides.

In some applications, variant nucleic acid molecules encode polypeptides that substantially maintain an XB3 functional activity. For other applications, variant nucleic acid molecules encode polypeptides that lack or feature a significant reduction in an XB3 functional activity. Where it is desired to retain a functional activity of native XB3, preferred variant nucleic acids feature silent or conservative nucleotide changes.

In other applications, variant XB3 polypeptides displaying substantial changes in one or more functional activities of native XB3 can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of native Xb3 within the invention are nucleic acids isolated from rice that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native Xb3, and encode polypeptides having as at least one functional activity in common with native XB3. Homologs of native Xb3 within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native Xb3, and encode polypeptides having at least one functional activity in common with native XB3. Naturally occurring allelic variants of Xb3 and homologs of Xb3 can be isolated by screening rice species and non-rice species (respectively) for a native XB3 functional activity (e.g., ability to bind XA21) using a yeast two-hybrid screen similarly to the method of identification of native Xb3 described herein, other assays described herein, or other techniques known in the art. The nucleotide sequence of such homologs and allelic variants can be determined by conventional DNA sequencing methods. Alternatively, public or non-proprietary nucleic acid databases can be searched to identify other nucleic acid molecules having a high percent (e.g., 70, 80, 90% or more) sequence identity to native Xb3. Once identified, these sequences can be incorporated into expression constructs that can be used in various assays such as those described herein to screen for those molecules that encode proteins which share or lack one or more functional activities of native XB3.

Non-naturally occurring Xb3 variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native Xb3, and encode polypeptides having as at least one functional activity in common with native XB3. Examples of non-naturally occurring Xb3 nucleic acids are those that encode a fragment of an XB3 protein, those that hybridize to native Xb3 or a complement of native Xb3 under stringent conditions, those that share at least 65% sequence identity with native Xb3 or a complement of native Xb3, and those that encode an XB3 fusion protein.

Nucleic acids encoding fragments of XB3 within the invention are those that encode, e.g., 2, 5, 10, 25, 50, 100, 150, 200, 250, 300, or more amino acid residues of XB3. Shorter oligonucleotides (e.g., those of 6, 12, 20, 30, 50, 100, 125, 150 or 200 base pairs in length) that encode or hybridize with nucleic acids that encode fragments of XB3 can be used as probes, primers, or antisense molecules. Longer polynucleotides (e.g., those of 300, 400, 500, 600, 700, 800, 900, 1000, 1100, 1200 or 1300 base pairs) that encode or hybridize with nucleic acids that encode fragments of XB3 can be used in place of native XB3 in applications where it is desired to modulate a functional activity of native XB3. Nucleic acids encoding fragments of XB3 can be made by enzymatic digestion (e.g., using a restriction enzyme) or chemical degradation of full length Xb3 or variants of Xb3.

Nucleic acids that hybridize under stringent conditions to the nucleic acid of SEQ ID NO:1 or the complement of SEQ ID NO:1 are also within the invention. For example, such nucleic acids can be those that hybridize to SEQ ID NO:1 or the complement of SEQ ID NO:1 under low stringency conditions, moderate stringency conditions, or high stringency conditions are within the invention. Preferred such nucleotide acids are those having a nucleotide sequence that is the complement of all or a portion of SEQ ID NO:1. Other variants of Xb3 within the invention are polynucleotides that share at least 65% (e.g., 65, 70, 75, 80, 85, 90, 91, 92, 93, 94, 95, 96, 97, 98, and 99%) sequence identity to SEQ ID NO:1 or the complement of SEQ ID NO:1. Nucleic acids that hybridize under stringent conditions to or share at least 65% sequence identity with SEQ ID NO:1 or the complement of SEQ ID NO:1 can be obtained by techniques known in the art such as by making mutations in native Xb3, by isolation from an organism expressing such a nucleic acid (e.g., a rice plant expressing a variant of native Xb3), or a non-rice plant (e.g., a tomato plant) expressing a homolog of native Xb3.

Nucleic acid molecules encoding XB3 fusion proteins are also within the invention. Such nucleic acids can be made by preparing a construct (e.g., an expression vector) that expresses an XB3 fusion protein when introduced into a suitable host. For example, such a construct can be made by ligating a first polynucleotide encoding an XB3 protein fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553–6556; Lemaitre et al. (1987) Proc. Natl. Acad. Sci. USA 84:648–652; PCT Publication No. WO 88/09810, published Dec. 15, 1988), hybridization-triggered cleavage agents. (See, e.g., Krol et al. (1988) BioTechniques 6:958–976) or intercalating agents. (See, e.g., Zon (1988) Pharm. Res. 5:539–549). To this end, the oligonucleotides may be conjugated to another molecule, e.g., a peptide, hybridization triggered cross-linking agent, transport agent, hybridization-triggered cleavage agent, etc.

Using the nucleotide of native Xb3 and the amino acid sequence of the XB3 polypeptides disclosed herein, those skilled in the art can create nucleic acid molecules that have minor variations in their nucleotide, by, for example, standard nucleic acid mutagenesis techniques or by chemical synthesis. Variant Xb3 nucleic acid molecules can be expressed to produce variant XB3 polypeptides.

Antisense, Ribozyme, Triplex, and RNA Interference Techniques

Another aspect of the invention relates to the use of purified antisense nucleic acids to inhibit expression of XB3. Antisense nucleic acid molecules within the invention are those that specifically hybridize (e.g. bind) under cellular conditions to cellular mRNA and/or genomic DNA encoding an XB3 protein in a manner that inhibits expression of the XB3 protein, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes an XB3 protein. Alternatively, the antisense construct can take the form of an oligonucleotide probe generated ex vivo which, when introduced into an XB3 expressing cell, causes inhibition of XB3 expression by hybridizing with an mRNA and/or genomic sequences coding for XB3. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of an XB3 encoding nucleotide sequence, are preferred.

Antisense approaches involve the design of oligonucleotides (either DNA or RNA) that are complementary to Xb3 mRNA. The antisense oligonucleotides will bind to Xb3 mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R. (1994) Nature 372:333). Therefore, oligonucleotides complementary to either the 5' or 3' untranslated, non-coding regions of an Xb3 gene could be used in an antisense approach to inhibit translation of endogenous Xb3 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of Xb3 mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantify the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Antisense oligonucleotides of the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Antisense oligonucleotides of the invention may also comprise at least one modified sugar moiety selected from the group including but not limited to arabinose, 2-fluoroarabinose, xylulose, and hexose; and may additionally include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) Nucl. Acids Res. 15:6625–6641). Such oligonucleotide can be a 2'-0-methylribonucleotide (Inoue et al. (1987) Nucl. Acids Res. 15:6131–6148), or a chimeric RNA-DNA analogue (Inoue et al. (1987) FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209), methylphosphonate oligonucleotides can be prepared by use of controlled pore glass polymer supports (Sarin et al. (1988) Proc. Natl. Acad. Sci. U.S.A. 85:7448–7451), etc.

The antisense molecules should be delivered into cells that express Xb3 in vivo. A number of methods have been developed for delivering antisense DNA or RNA into cells. For instance, antisense molecules can be introduced directly into the tissue site using bombardment-based methodology (see, e. g., Christou P., Plant Mol Biol 35: 197 (1997)) or by Agrobacterium-mediated transformation (see, e.g., Hiei et al., Plant Mol. Biol. 35: 205 (1997)). Alternatively, modified antisense molecules, designed to target the desired cells (e.g., antisense linked to peptides or antibodies that specifically bind receptors or antigens expressed on the target cell surface) can be used.

However, because it is often difficult to achieve intracellular concentrations of the antisense sufficient to suppress translation on endogenous mRNAs, a preferred approach utilizes a recombinant DNA construct in which the antisense oligonucleotide is placed under the control of a strong promoter (e.g., the maize ubiquitin promoter). The use of such a construct to transform rice plants will result in the transcription of sufficient amounts of single stranded RNAs that will form complementary base pairs with the endogenous Xb3 transcripts and thereby prevent translation of Xb3 mRNA.

Ribozyme molecules designed to catalytically cleave Xb3 mRNA transcripts can also be used to prevent translation of Xb3 mRNA and expression of XB3 (See, e.g., PCT Publication No. WO 90/11364, published Oct. 4, 1990; Sarver et al. (1990) Science 247:1222–1225 and U.S. Pat. No. 5,093, 246). While ribozymes that cleave mRNA at site specific recognition sequences can be used to destroy Xb3 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585–591. There are hundreds of potential hammerhead ribozyme cleavage sites within the nucleotide sequence of native Xb3. Preferably the ribozyme is engineered so that the cleavage recognition site is located near the 5' end of Xb3 mRNA; i.e., to increase efficiency and minimize the intracellular accumulation of non-functional mRNA transcripts. Ribozymes within the invention can be delivered to a cell using a vector as described below.

Endogenous Xb3 gene expression can also be reduced by inactivating or "knocking out" the Xb3 gene or its promoter using targeted homologous recombination. See, e.g., Kempin et al., Nature 389: 802 (1997); Smithies et al. (1985) Nature 317:230–234; Thomas and Capecchi (1987) Cell 51:503–512; and Thompson et al. (1989) Cell 5:313–321. For example, a mutant, non-functional Xb3 variant (or a completely unrelated DNA sequence) flanked by DNA homologous to the endogenous Xb3 gene (either the coding regions or regulatory regions of the XB3 gene) can be used, with or without a selectable marker and/or a negative selectable marker, to transfect cells that express XB3 in vivo.

Alternatively, endogenous Xb3 gene expression might be reduced by targeting deoxyribonucleotide sequences complementary to the regulatory region of the Xb3 gene (i.e., the Xb3 promoter and/or enhancers) to form triple helical structures that prevent transcription of the Xb3 gene in target cells. (See generally, Helene, C. (1991) Anticancer Drug Des. 6(6):569–84; Helene, C., et al. (1992) Ann. N.Y. Acad. Sci. 660:27–36; and Maher, L. J. (1992) Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Another technique that may be employed to modulate XB3 expression is RNA interference (RNAi). Chuang and Meyerowicz, Proc. Nat'l Acad. Sci. USA, 97:4985 (2000). In this technique, double-stranded RNA (dsRNA)-expressing constructs are introduced into a plant using, e.g., Agrobacterium mediated transformation. In this manner, such dsRNA is persistent and inherited. By selecting appropriate sequences (e.g., those corresponding to Xb3), expression of dsRNA can interfere with accumulation of endogenous mRNA encoding a target protein (e.g., XB3).

In another method for modulating XB3 function, nucleic acid molecules encoding dominant negative mutants of XB3 are used to inhibit the function of native XB3 by competing with native XB3. For example, overexpression of a nucleic acid encoding only the ankyrin domain of XB3 (the domain that binds XA21) could be performed to reduce interaction of native XB3 with XA21.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Probes and Primers

The invention also includes oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods. Probes and primers within the invention are generally 15 nucleotides or more in length, preferably 20 nucleotides or more, more preferably 25 nucleotides, and most preferably 30 nucleotides or more. Preferred probes and primers are those that hybridize to the native Xb3 sequence (SEQ ID NO:1) under high stringency conditions, and those hybridize Xb3 homologs under at least moderately stringent conditions. Preferably, probes and primers according to the present invention have complete sequence identity with the native rice Xb3 sequence, although probes differing from the rice Xb3 sequence and that retain the ability to hybridize to native Xb3 sequences under stringent conditions may be designed by conventional methods. Primers and probes based on the native rice Xb3 sequences disclosed herein can be used to confirm (and, if necessary, to correct) the disclosed Xb3 sequences by conventional methods, e.g., by re-cloning and sequencing a rice Xb3 cDNA.

Vectors for Expressing XB3

Natural or synthetic nucleic acids according to the present invention can be incorporated into recombinant nucleic acid constructs, typically DNA constructs, capable of introduction into and replication in a host cell. Such a construct preferably is a vector that includes a replication system and sequences that are capable of transcription and translation of a polypeptide-encoding sequence in a given host cell. For the practice of the present invention, conventional compositions and methods for preparing and using vectors and host cells are employed, as discussed, e.g., in Sambrook et al., supra, or Ausubel et al., supra.

Expression of Xb3 genes in plants is achieved by introducing into a plant a nucleic acid sequence containing an Xb3 gene encoding an XB3 polypeptide. A number of vectors suitable for stable transformation of plant cells or for the establishment of transgenic plants are known. See, e.g., Pouwels et al., Cloning Vectors: A Laboratory Manual, 1985, Supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include (1) one or more cloned plant genes under the transcriptional control of 5' and 3' regulatory sequences and (2) a dominant selectable marker. Such plant expression vectors may also contain, if desired, a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

An example of a useful plant promoter which could be used to express a plant resistance gene according to the invention is a caulimovirus promoter, e.g., the cauliflower mosaic virus (CaMV) 35S promoter. These promoters confer high levels of expression in most plant tissues, and are generally not dependent on the particular encoded proteins to be expressed. CaMV is a source for both the 35S and 19S promoters. In most tissues of transgenic plants, the CaMV 35S promoter is a strong promoter. See, e.g., Odel et al., Nature 313:810, (1985); Dekeyser et al., Plant Cell 2:591, (1990); Terada and Shimamoto, Mol. Gen. Genet. 220:389, (1990). Another such promoter that is particularly preferred for expression in rice is the maize ubiquitin promoter. Christensen and Quail, Transgenic Res., 5:213–218 (1996). Other plant promoters that may be useful in the invention are known. See, e.g., An et al., Plant Physiol. 88:547, (1988); Fromm et al., Plant Cell 1:977, (1989); Callis et al., Plant Physiol. 88: 965, (1988); Kuhlemeier et al., Plant Cell 1: 471, (1989); Schaffner and Sheen, Plant Cell 3: 997, (1991); Simpson et al., EMBO J. 4: 2723, (1985); Marcotte et al., Plant Cell 1:969, (1989); Siebertz et al., Plant Cell 1:961, (1989); Roshal et al., EMBO J. 6:1155, (1987); Schernthaner et al., EMBO J. 7:1249, (1988); and Bustos et al., Plant Cell 1:839, (1989)).

Plant expression vectors may also include RNA processing signals such as introns, which have been shown to be important for efficient RNA synthesis and accumulation. Callis et al., Genes and Dev. 1: 1183, (1987). The location of the RNA splice sequences can influence the level of transgene expression in plants. In view of this fact, an intron may be positioned upstream or downstream of an XB3 polypeptide-encoding sequence in the transgene to modulate levels of gene expression.

Expression vectors within the invention may also include regulatory control regions which are generally present in the 3' regions of plant genes. See, e.g., Thornburg et al., Proc. Natl Acad. Sci USA 84: 744, (1987); An et al., Plant Cell 1: 115, (1989). For example, a 3' terminator region may be included in the expression vector to increase stability of the mRNA. For instance, 3' terminators derived from octopine or nopaline synthase genes could be used.

Plant expression vector within the invention preferably contain a selectable marker gene used to identify the cells that have become transformed. Suitable selectable marker genes for plant systems include genes encoding enzymes that produce antibiotic resistance (e.g., those conferring resistance to hygromycin, kanamycin, bleomycin, G418, streptomycin or spectinomycin) or herbicide resistance (e.g., phosphinothricin acetyltransferase which confers resistance to the herbicide Basta® (Hoechst AG, Frankfurt, Germany). A useful strategy for selection of transformants for herbicide resistance is described in Vasil I. K., Cell Culture and Somatic Cell Genetics of Plants, Vol I, II, III Laboratory Procedures and Their Applications Academic Press, New York, 1984.

Cells Transformed with Xb3

Upon construction of the plant expression vector, several standard methods are known for introduction of the recombinant genetic material into the host plant for the generation of a transgenic plant. Examples of such methods include (1) Agrobacterium-mediated transformation (*A. tumefaciens* or *A. rhizogenes*) (see, e.g., Lichtenstein and Fuller In: Genetic Engineering, vol 6, PWJ Rigby, ed, London, Academic Press, 1987; and Lichtenstein, C. P., and Draper, J,. In: DNA Cloning, Vol II, D. M. Glover, ed, Oxford, IRI Press, 1985), (2) the particle delivery system (see, e.g., Gordon-Kamm et al., Plant Cell 2:603, (1990); or BioRad Technical Bulletin 1687, supra), (3) microinjection protocols (see, e.g., Green et al., Plant Tissue and Cell Culture, Academic Press, New York, 1987), (4) polyethylene glycol (PEG) procedures (see, e.g., Draper et al., Plant Cell Physiol 23:451, (1982); or e.g., Zhang and Wu, Theor. Appl. Genet. 76:835, (1988)), (5) liposome-mediated DNA uptake (see, e.g., Freeman et al., Plant Cell Physiol 25: 1353, (1984)), (6) electroporation protocols (see, e.g., Gelvin et al supra; Dekeyser et al. supra; or Fromm et al Nature 319: 791, (1986)), and (7) the vortexing method (see, e.g., Kindle, K., Proc. Natl. Acad. Sci., USA 87:1228, (1990)). Agrobacterium-mediated plant transformation is typically carried out in two phases. First, all the cloning and DNA modification steps are done in *E. coli*, and the plasmid containing the gene construct of interest is transferred by conjugation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, e.g., streptomycin, and the other that will express in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of Agrobacterium, delimit the region that will be transferred to the plant.

In another example, plant cells may be transformed by shooting into the cell tungsten microprojectiles on which cloned DNA is precipitated. In the Biolistic Apparatus (Bio-Rad, Hercules, Calif.) used for the shooting, a gunpowder charge (0.22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transgenic Plants

Transgenic plants within the invention can be made by regenerating plant cells transformed with a plant expression vector by standard plant tissue culture techniques. See, e.g., in Vasil supra; Green et al., supra; Weissbach and Weissbach, supra; and Gelvin et al., supra. For example, a vector carrying a selectable marker gene (e.g., kanamycin resistance), a cloned Xb3 gene under the control of its own promoter and terminator or, if desired, under the control of exogenous regulatory sequences such as the 35S CaMV promoter and the nopaline synthase terminator is transformed into Agrobacterium. Transformation of leaf tissue with vector-containing Agrobacterium is carried out as described in L. L. Ilag, R. C. Yadav, N. Huang, P. C. Ronald, and F. M. Ausubel, Plant Molecular Biology (submitted). See also, Horsch et al. (Science 227: 1229, (1985)). Putative transformants are selected after a few weeks (e.g., 3 to 5 weeks) on plant tissue culture media containing kanamycin (e.g. 100 $\mu$g/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less media and grown in a greenhouse. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra).

Transgenic plants expressing the selectable marker are then screened for transmission of the transgene DNA by standard immunoblot and DNA and RNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using XB3 polypeptide-specific antibodies (see below and Ausubel et al., supra). In addition, in situ hybridization and immunocytochemistry according to standard protocols can be done using transgene-specific nucleotide probes and antibodies, respectively, to localize sites of expression within transgenic tissue.

XB3 Polypeptides

In another aspect, the present invention provides a purified XB3 polypeptide encoded by a nucleic acid of the invention. A preferred form of XB3 is a purified native XB3 polypeptide that has the deduced amino acid sequence shown in FIG. 1B (SEQ ID No. 2). Variants of native XB3 such as fragments, analogs and derivatives of native XB3 are also within the invention. Such variants include, e.g., a polypeptide encoded by a naturally occurring allelic variant of native Xb3, a polypeptide encoded by a homolog of native Xb3, and a polypeptide encoded by a non-naturally occurring variant of native Xb3.

XB3 variants have a peptide sequence that differs from native XB3 in one or more amino acids. The peptide sequence of such variants can feature a deletion, addition, or substitution of one or more amino acids of a native XB3 polypeptide. Amino acid insertions are preferably of about 1 to 4 contiguous amino acids, and deletions are preferably of about 1 to 10 contiguous amino acids. In some applications, variant XB3 polypeptides substantially maintain a native XB3 functional activity. For other applications, variant XB3 polypeptides lack or feature a significant reduction in an XB3 functional activity. Where it is desired to retain a functional activity of native XB3, preferred XB3 variants can be made by expressing nucleic acid molecules within the invention that feature silent or conservative changes. Variant XB3 polypeptides with substantial changes in functional activity can be made by expressing nucleic acid molecules within the invention that feature less than conservative changes.

XB3 fragments corresponding to one or more particular motifs and/or domains or to arbitrary sizes, for example, at least 5, 10, 25, 50, 75, 100, 125, 150, 175, 200, 250, 300, and 350 amino acids in length are within the scope of the present invention. Isolated peptidyl portions of XB3 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an XB3 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of native XB3.

Another aspect of the present invention concerns recombinant forms of the XB3 proteins. Recombinant polypeptides preferred by the present invention, in addition to native XB3, are encoded by a nucleic acid that has at least 85% sequence identity (e.g., 85, 86, 87, 88, 89, 90, 91, 92, 93, 94, 95, 96, 97, 98, 99, 100%) with the amino acid sequence of SEQ ID NO:2. In a preferred embodiment, an XB3 protein of the present invention is a rice XB3 protein. In particularly preferred embodiment, an XB3 protein has one or more functional activities of native XB3.

XB3 variants can be generated through various techniques known in the art. For example, XB3 variants can be made by mutagenesis, such as by introducing discrete point mutation (s), or by truncation. Mutation can give rise to an XB3 variant having substantially the same, or merely a subset of the biological activity of native XB3. Alternatively, antagonistic forms of the protein can be generated which are able to inhibit the function of the naturally occurring form of the protein, such as by competitively binding to a downstream or upstream member of the XB3 signaling cascade such as XA21. In addition, agonistic forms of the protein may be generated which are constitutively active (e.g., by removing a phosphorylation site on native XB3). Other variants of XB3 that can be generated include those that are resistant to proteolytic cleavage, as for example, due to mutations which alter ubiquitination or other enzymatic targeting associated with the protein. Whether a change in the amino acid sequence of a peptide results in an XB3 variant having one or more functional activities of native XB3 can be readily determined by testing the variant for a native XB3 functional activity in one or more of the assays described herein.

As another example, XB3 variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential XB3 sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. AG Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) Proc. Natl. Acad. Sci. USA 89:2429–2433; Devlin et al. (1990) Science 249: 404–406; Cwirla et al. (1990) Proc. Natl. Acad. Sci. USA 87: 6378–6382; as well as U.S. Pat. Nos. 5,223, 409, 5,198,346, and 5,096,815).

Similarly, a library of coding sequence fragments can be provided for an Xb3 clone in order to generate a variegated population of XB3 fragments for screening and subsequent selection of fragments having one or more native XB3 functional activities. A variety of techniques are known in the art for generating such libraries, including chemical synthesis. In one embodiment, a library of coding sequence fragments can be generated by (i) treating a double stranded PCR fragment of an XB3 coding sequence with a nuclease under conditions wherein nicking occurs only about once per molecule; (ii) denaturing the double stranded DNA; (iii) renaturing the DNA to form double stranded DNA which car include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of XB3 variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate XB3 sequences created by combinatorial mutagenesis techniques.

In one embodiment, cell based assays can be exploited to analyze the variegated XB3 library. For instance, the library of expression vectors can be transfected into a plant cell that ordinarily mediates an HR via XA21 in response to an avirulent pathogen. The transfected cells are then infected with a pathogen (e.g., avirulent or virulent) and the effect on the HR can be monitored. Plasmid DNA can then be recovered from the cells which score for inhibition, or alternatively, potentiation of the HR, and the individual clones further characterized.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, techniques such as recursive ensemble mutagenesis (REM) that allow one to avoid the very high proportion of non-functional proteins in a random library and simply enhance the frequency of functional proteins (thus decreasing the complexity required to achieve a useful sampling of sequence space) can be used. REM is an algorithm which enhances the frequency of functional mutants in a library when an appropriate selection or screening method is employed (Arkin and Yourvan (1992) Proc. Natl. Acad. Sci. USA 89:7811–7815; Yourvan et al. (1992) Parallel Problem Solving from Nature, 2., In Maenner and Manderick, eds., Elsevier Publishing Co., Amsterdam, pp. 401–410; Delgrave et al. (1993) Protein Engineering 6(3):327–331).

The invention also provides for reduction of XB3 proteins to generate mimetics, e.g. peptide or non-peptide agents, which are able to disrupt binding of a XB3 polypeptide of the present invention with either upstream or downstream components of the resistance signaling cascade such as XA21 or other binding proteins or interactors. Thus, the mutagenic techniques described can also be used to map which determinants of XB3 participate in protein-protein interactions involved in, for example, binding of XB3 to proteins which may function upstream (including both activators and repressors of its activity) of XB3 or to proteins or nucleic acids which may function downstream of XB3, and whether such molecules are positively or negatively regulated by XB3. To illustrate, the critical residues of XB3 which are involved in molecular recognition of, for example, XB3 or other components upstream or downstream of XB3 can be determined and used to generate XB3-derived peptidomimetics which competitively inhibit binding of XB3 with that moiety. By employing, for example, scanning mutagenesis to map the amino acid residues of XB3 that are involved in binding other extracellular proteins, peptidomimetic compounds can be generated which mimic those residues of native XB3. Such mimetics may then be used to interfere with the normal function of an XB3 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopepitides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J. Chem. Soc. Perkin. Trans. 1:1231), and b-aminoalcohols (Gordon et al. (1985) Biochem. Biophys. Res. Commun. 126:419; and Dann et al. (1986) Biochem. Biophys. Res. Commun. 134:71). XB3 polypeptides may also be chemically modified to create XB3 derivatives by forming covalent or aggregate conjugates with other chemical moieties, such as glycosyl groups, lipids, phosphate, acetyl groups and the like. Covalent derivatives of XB3 can be prepared by linking the chemical moieties to functional groups on amino acid sidechains of the protein or at the N-terminus or at the C-terminus of the polypeptide.

The present invention further pertains to methods of producing the subject XB3 polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant XB3 polypeptide can be isolated from host cells using techniques known in the art for purifying proteins including ion-exchange chromatography, gel filtration chromatography, ultrafiltration, electrophoresis, and immunoaffinity purification with antibodies specific for such peptide.

For example, after XB3 has been expressed in any cell or in a transgenic plant (e.g., as described above), it can be isolated using any immuno-affinity chromatography. For instance, an anti-XB3 antibody (e.g., produced as described below) can be immobilized on a column chromatography matrix, and the matrix can be used for immuno-affinity chromatography to purify XB3 from cell lysates by standard methods (see, e.g., Ausubel et al., supra). After immuno-affinity chromatography, XB3 can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, XB3 is expressed as a fusion protein containing an affinity tag (e.g., GST) that facilitates its purification.

Anti-XB3 Antibodies

XB3 polypeptides (or immunogenic fragments or analogs thereof) can be used to raise antibodies useful in the invention. Such polypeptides can be produced by recombinant techniques or synthesized as described above. In general, XB3 polypeptides can be coupled to a carrier protein, such as KLH, as described in Ausubel et al., supra, mixed with an adjuvant, and injected into a host mammal. Antibodies produced in that animal can then be purified by peptide antigen affinity chromatography. In particular, various host animals can be immunized by injection with a XB3 polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and *Corynebacterium parvum*.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the XB3 polypeptides described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific XB3 recognition by Western blot or immunoprecipitation analysis by standard methods, for example, as described in Ausubel et al., supra. Antibodies that specifically recognize and bind to XB3 are useful in the invention. For example, such antibodies can be used in an immunoassay to monitor the level of XB3 produced by a mammal (e.g., to determine the amount or subcellular location of XB3).

Preferably, XB3 selective antibodies of the invention are produced using fragments of the XB3 polypeptide that lie outside highly conserved regions and appear likely to be antigenic, by criteria such as high frequency of charged residues. Cross-reactive anti-XB3 antibodies are produced using a fragment of XB3 that is conserved amongst members of this family of proteins. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant XB3 polypeptides or control proteins, such as glucocorticoid receptor, CAT, or luciferase.

The antibodies of the invention can be used, for example, in the detection of XB3 in a biological sample. Antibodies also can be used in a screening assay to measure the effect of a candidate compound on expression or localization of XB3. Additionally, such antibodies can be used to interfere with the interaction of XB3 and other molecules that bind XB3 (e.g., XA21).

Techniques described for the production of single chain antibodies (U.S. Pat. Nos. 4,946,778, 4,946,778, and 4,704,692) can be adapted to produce single chain antibodies against an XB3 polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

Proteins that Associate with XB3

The invention also features methods for identifying polypeptides that can associate with XB3. Any method that is suitable for detecting protein-protein interactions can be employed to detect polypeptides that associate with XB3. Among the traditional methods that can be employed are co-immuno-precipitation, crosslinking, and co-purification through gradients or chromatographic columns of cell lysates or proteins obtained from cell lysates and the use of XB3 to identify proteins in the lysate that interact with XB3. For these assays, the XB3 polypeptide can be a full length XB3, a particular domain of XB3, or some other suitable XB3 polypeptide. Once isolated, such an interacting protein can be identified and cloned and then used, in conjunction with standard techniques, to alter the activity of the XB3 polypeptide with which it interacts. For example, at least a portion of the amino acid sequence of a protein that interacts with XB3 can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and "PCR Protocols: A Guide to Methods and Applications," Innis et al., eds. Academic Press, Inc., NY, 1990).

Additionally, methods can be employed that result directly in the identification of genes that encode proteins that interact with XB3. These methods include, for example, screening expression libraries, in a manner similar to the well known technique of antibody probing of lgt11 libraries, using labeled XB3 polypeptide or a XB3 fusion protein, for example, a XB3 polypeptide or domain fused to a marker such as an enzyme, fluorescent dye, a luminescent protein, or to an IgFc domain.

There are also methods available that can detect protein-protein interaction in vivo. For example, as described herein the two-hybrid system can be used to detect such interactions in vivo. See, Chien et al., Proc. Natl. Acad. Sci. USA 88:9578, 1991). Briefly, as one example of utilizing such a system, plasmids are constructed that encode two hybrid proteins: one plasmid includes a nucleotide sequence encoding the DNA-binding domain of a transcription activator protein fused to a nucleotide sequence encoding XB3, an XB3 variant, or a XB3 fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomyces cerevisiae that contains a reporter gene (e.g., HBS or LacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, XB3 may be used as the bait. Total genomic or cDNA sequences are fused to the DNA encoding an activation domain. This library and a plasmid encoding a hybrid of bait XB3 fused to the DNA-binding domain are co-transformed into a yeast reporter strain, and the resulting transformants are screened for those that express the reporter gene. For example, a bait Xb3 gene sequence, such as that encoding XB3 or a domain of XB3 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line and plants from which proteins that interact with bait XB3 are to be detected can be made using methods routinely practiced in the art. According to the particular system described herein, for example, the cDNA fragments can be inserted into a vector such that they are translationally fused to the transcriptional activation domain of GAL4. This library can be co-transformed along with the XB3-GAL4 encoding fusion plasmid into a yeast strain which contains a lacZ gene driven by a promoter which contains GAL4 activation sequence. A cDNA encoded protein, fused to GAL4 transcriptional activation domain, that interacts with bait X3 will reconstitute an active GAL4 protein and thereby drive expression of the HIS3 gene. Colonies that express HIS3 can then be purified from these strains and used to produce and isolate bait XB3-interacting proteins using techniques routinely practiced in the art.

Detection of XB3 or Nucleic Acid Molecules Encoding XB3

The invention encompasses methods for detecting the presence of XB3 protein or Xb3 nucleic acid in a biological sample as well as methods for measuring the level of XB3 protein or Xb3 nucleic acid in a biological sample. Such methods are useful for examining plant intracellular signaling pathways associated with disease resistance.

An exemplary method for detecting the presence or absence of XB3 in a biological sample involves obtaining a biological sample from a test plant (or plant cell) and contacting the biological sample with a compound or an agent capable of detecting an XB3 polypeptide or a nucleic acid encoding an XB3 polypeptide (e.g., mRNA or genomic DNA). A preferred agent for detecting a nucleic acid encoding an XB3 polypeptide is a labeled nucleic acid probe capable of hybridizing to the nucleic acid encoding the XB3 polypeptide. The nucleic acid probe can be, for example, all or a portion of Xb3 itself (e.g., a nucleic acid molecule having the sequence of SEQ ID NO:1) or all or a portion of a complement of Xb3. Similarly, the probe can also be all or a portion of an Xb3 variant, or all or a portion of a complement of an Xb3 variant. For instance, oligonucleotides at least 15, 30, 50, 100, 250, or 500 nucleotides in length that specifically hybridize under stringent conditions to native Xb3 or a complement of native Xb3 can be used as probes within the invention.

A preferred agent for detecting an XB3 polypeptide is an antibody capable of binding to an XB3 polypeptide, preferably an antibody with a detectable label. Such antibodies can be polyclonal, or more preferably, monoclonal. An intact antibody, or a fragment thereof (e.g., Fab or F(ab')$_2$) can be used.

Detection methods of the invention can be used to detect an mRNA encoding XB3, a genomic DNA encoding XB3, or an XB3 polypeptide in a biological sample in vitro as well as in vivo. For example, in vitro techniques for detection of mRNAs encoding XB3 include Northern hybridizations and in situ hybridizations. In vitro techniques for detection of a XB3 polypeptide include enzyme linked immunosorbent assays (ELISAs), Western blots, immunoprecipitations and immunofluorescence. In vitro techniques for detection of genomic DNA encoding XB3 include Southern hybridizations. Furthermore, in vivo techniques for detection of a XB3 polypeptide include introducing into a plant or plant cell labeled anti-XB3 antibody. For example, the antibody can be labeled with a radioactive marker whose presence and location in a plant can be detected by standard imaging techniques.

Assays for Compounds that Interfere with XB3 and XA21 Binding

The invention can be used to screen candidate substances for the ability to inhibit the interaction of XA21 with XB3. In an exemplary screening method, the two-hybrid expression system is used to screen for substances capable of inhibiting XA21-XB3 interaction in vivo. In this system, a GAL4 binding site, linked to a reporter gene such as lacZ, is contacted in the presence and absence of a candidate substance with a GAL4 binding domain linked to an XB3 fragment and a GAL4 transactivation domain II linked to an XA21 fragment. Expression of the reporter gene is monitored, and a decrease in its expression is an indication that the candidate substance inhibits the interaction of XA21 with XB3. One of ordinary skill in the art will recognize that other screening assays are known and can be used to identify candidate substances that inhibit XA21-XB3 interaction.

In another screening method, one of the protein components of the XA21-XB3 binding complex, such as XA21, an XB3-binding fragment of XA21, XB3, or an XA21-binding fragment of XB3 is immobilized. Polypeptides can be immobilized using methods known in the art. Such methods include adsorption onto a plastic microliter plate or specific binding of a glutathione-S-transferase (GST)-fusion protein to a polymeric bead containing glutathione. For example, a GST-XB3 fusion protein can be bound to glutathione-Sepharose beads. The immobilized protein (e.g., GST-XB3) is then contacted with the labeled protein to which it binds (XA21 in this example) in the presence and absence of a candidate substance. Unbound protein can be removed by washing. The complex can then be solubilized and analyzed to determine the amount of bound (labeled) protein. A decrease in binding is an indication that the candidate substance inhibits the interaction of XA21 and XB3. A variation of the above-described screening method can be used to screen for other classes of candidate substances, e.g., those that disrupt previously-formed XA21-XB3 complexes. In this variation, a complex containing XA21 (or an XB3-binding XA21 fragment) bound to XB3 (or an XA21-binding XB3 fragment) is immobilized and contacted with a candidate compound. Detection of disruption of the XA21-XB3 complex by the candidate substance identifies the candidate substance as a potential modulator of XA21-mediated cellular events.

The present invention is further illustrated by the following specific examples. The examples are provided for illustration only and are not to be construed as limiting the scope or content of the invention in any way.

EXAMPLES

Example 1

Isolation and Identification of the Xb3 Gene and XB3 Protein

To identify XA21-interacting proteins, a yeast two-hybrid rice cDNA library was screened using the XA21 kinase as bait. To make the BD-XA21 construct for yeast two-hybrid screening, a polynucleotide encoding the kinase domain of XA21 (aa677 to aa1025) was amplified by using polymerase chain reaction (PCR), verified by sequencing, and cloned into the two-hybrid vector pPC97 carrying the GAL4 BD domain. See, P. M. Chevray, and D. Nathans, Proc. Natl. Acad. Sci. U.S.A. 89,5789 (1992). The resulting vector construct, termed pPC97XA21, was transformed into the yeast strain CG1945. The CG1945 cells carrying pPC97XA21 were then transformed with a yeast two-hybrid library constructed from poly (A)$^+$ mRNA harvested from two-week seedlings of Oryza sativa ssp. Japonica var. Taipei309 made with the pPC86 vector. Yin et al., EMBO J. 16, 5247 (1997). The library was obtained from R. Beachy at the Donald Danforth Plant Science Center, St. Louis, Mo. Transformation efficiency was estimated by plating an aliquot of transformation mixtures onto SD lacking leucine and tryptophan. Candidates selected onto SD medium lacking leucine, tryptophan, and histidine were subjected to β-galactosidase assays as described by the manufacture's procedure of the MATCHMAKER GAL4 system (Clontech, Palo Alto, Calif.).

From more than 25 million transformants, seven classes of proteins were found to interact with the XA21 kinase in the yeast two-hybrid system. Plasmids were recovered from cells showing the His$^+$/Lac$^+$ phenotypes (i.e., cells from colonies that turned blue when subjected to colony-lift assay) and sequenced to determine their identity. One such plasmid was isolated and named pPC86XB3. Using primers on pPC86 and conventional sequencing techniques, the nucleotide sequence of the cDNA included in this plasmid, including the portion encoding the protein that interacted with XA21 (i.e., Xb3) was obtained. The nucleotide sequence of Xb3 is shown in FIG. 1A (SEQ ID NO:1), and has been deposited with GenBank as Accession number AF272860.

Referring now to FIG. 1B, from the nucleotide sequence of the identified nucleotide sequence, it was deduced that Xb3 encodes a protein (native XB3) of 450 amino acids (aa). (Single-letter abbreviations for the amino acid residues are as follows: A, Ala; C, Cys; D, Asp; E, Glu; F, Phe; G, Gly; H, His; I, Ile, K, Lys; L, Leu; M, Met; N, Asn; P, Pro; Q, Gln; R, Arg; S, Ser; T, Thr; V, Val; W, Trp; and Y, Tyr). The N-terminal domain (Domain I) of native XB3 (aa 1–10) contains a myristoylation site suggesting that native XB3 may be localized in plasma membrane. See, M. D. Resh, Biochim Biophys Acta. 1451, 1 (1999); H. Taniguchi, Biophys. Chem. 82, 129 (1999). XB3 domain II (aa 11–305) contains 8 imperfect copies of ankyrin repeats (see, S. G. Sedgwick and S. J. Smerdon, Trends Biochem. Sci. 24, 311 (1999)). Domain IV (aa 319–385) contains a RING finger motif. Domain III (aa 306–318) and V (aa 386–450) are of unknown function.

Referring now to FIG. 1C, a BLAST search using the RING finger sequence as a query identified the human and mouse protooncoproteins Cb1 and the baculovirus inhibitor of apoptosis. The SwissProt database was searched with the BlastP algorithm [S. F. Altschul, G. Warren, W. Miller, E. W. Myers, D. J. Lipman, J. Mol. Biol. 215,403 (1990)]. The Wisconsin sequence analysis program GAP was used to calculate the percent identity of proteins. The GenBank accession numbers for human c-Cb1 and Baculovirus Inhibitor of Apoptosis are P22681 and P41436, respectively. These proteins regulate cell signaling through ubiquitin-mediated protein degradation. Joazeiro et al., Molecular Cell 4, 1029 (1999); Yoon et al., Science 269, 1102 (1995); and Yang et al., Science 288, 874 (2000), suggesting that the RING finger domain of native XB3 might have a similar function.

Example 2

Characterization of XB3-XA21 Interaction

The specificity of the XB3/XA21 interaction was further characterized using the yeast two-hybrid system as described in Example 1 to examine the ability of native XB3 to interact with an XA21 variant, and the ability of two truncation mutants of native XB3 to interact with XA21. The XA21 variant assessed was XA21C, a protein encoded by a member of the Xa21 gene family that shares 78.5% sequence identity with native XA21 kinase. Song et al., Plant Cell 9,1279 (1997). XA21C was identified in a search of the SwissProt database using the BlastP algorithm (S. F. Altschul, G. Warren, W. Miller, E. W. Myers, D. J. Lipman, J Mol. Biol. 215, 403 (1990), and The Wisconsin sequence analysis program, GAP, to calculate percent sequence identity. XA21C has no known physiological function, but transgenic plants expressing Xa21C (i.e., the gene encoding XA21C) are known to be susceptible to all tested races of Xoo, not just virulent strains. Song et al., Plant Cell 9,1279 (1997). To make the construct encoding the BD-XA21C fusion for yeast two-hybrid screening, a polynucleotide encoding the XA21C kinase domain was amplified using PCR (primers for PCR: 5' GTCGACCAGATCTCATAA-GAGAAGAA AGA 3' (SEQ ID NO:3) and 5' GTCGAC-GAATGAAATCAGT TGTGAAGGGTAC 3' (SEQ ID NO:4)), verified by sequencing, and cloned into the Sal I site of the two-hybrid vector pPC97 carrying the GAL4 BD domain. See, Chevray, and Nathans, supra. The results showed that GAL4 DNA binding domain-XA21C (BD-XA21C) fusion protein did not bind to AD-XB3 in the yeast system, suggesting the interaction between XB3 and native XA21 is specific. The GAL4 DNA binding domain-native XA21 (BD-XA21) fusion protein interacted with the GAL4 activation domain-XB3 (AD-XB3) protein, but not with the AD itself.

To determine which region of native XB3 is responsible for binding to XA21, two truncated forms of XB3 (XB3-N and XB3-C) spanning either the N- or C-terminal half of native XB3 were prepared (see FIG. 2). To make XB3-N and XB-3-C, the pPC86XB3 plasmid carrying the full-length cDNA of XB3 was digested with EcoRI and Not I to release the C-terminus of XB3. After fill-in of the ends, the plasmid containing the N-terminus was self-ligated to make XB3-N. To construct XB3-C, the EcoR I-Not I fragment carrying the C-terminal half of XB3 was ligated to the corresponding sites of the two-hybrid vector pPC86 containing the GAL4 transcription activation domain (Yin et al., EMBO J. 16, 5247 (1997). XB3-N carried 5½ of the eight ankyrin repeats, and XB3-C spanned the last 2½ of the ankyrin repeats, the RING finger domain, and the C-terminal tail. Neither of these mutants interacted with XA21 in the yeast two-hybrid assay. Thus, either the entire native XB3 protein or the full-length ankyrin repeats are required for binding to XA21 in the yeast two-hybrid system.

An in vitro binding assay was performed as described below to test whether the ankyrin domain of native XB3 physically binds to XA21. A polynucleotide encoding XA21 was PCR amplified from GTK-XA21 carrying the XA21 kinase domain with the primers: 5' GGATCCGTCGACCA CAAGAGAACTAAAAAGGGAGC 3' (SEQ ID NO:5) and 5' GGATCCGTCGACCCCGGG CAGAAGTCGATCT-GAAGTGTGGCA 3' (SEQ ID NO:6) and cloned into the BamHI site of pET-28a (Novagen, Madison, Wis.). This plasmid was expressed and the resulting XA21 protein labeled with $^{35}$S using the in vitro transcription and translation (TnT) kit (Promega, Madison, Wis.).

Because the full-length XB3 was poorly expressed as an MBP (Maltose Binding Protein) fusion protein, a cDNA encoding aa 1–428 of XB3 (missing the last 22 aa) was cloned in-frame into the BamHI-Hind III sites of pMAL-c2X (New England Biolabs, Beverly, Mass.) to make MBP-XB3. A polynucleotide encoding the ankyrin domain of XB3 was PCR amplified with primers 5' GGATCCATGATATC-CATGGGTCACGGTGTC 3' (SEQ ID NO:7) and 5' CGG-GATCCGATATCAGATGCAGCAAAGCTCC 3' (SEQ ID NO:8), and then cloned into the BamH I site of pMAL-c2X. Using these constructs, XB3 and the ankyrin repeats of XB3 were expressed as MBP fusions, and these fusion proteins (respectively termed MBP-XB3 and MBP-XB3 ankyrin) were bound to amylose resin as described by the manufacture's procedure of the Protein Fusion & Purification (pMAL™) system (New England Biolabs, Beverly, Mass.). Native MBP bound to amylose resin was used as a control.

The $^{35}$S-labeled XA21 kinase was then incubated with resin-bound MBP or MBP fusion proteins (1 ug) in the binding buffer [20 mM Hepes (pH 7.4), 1 mM EDTA, 5 mM MgCl$_2$, 1 mM DTT, 0.1% Triton X-100, 1 mg/ml BSA, 1× complete protease inhibitors (Roche Diagnostics)] for 120 min at 4° C. with gentle shaking. After washing with the washing buffer [20 mM Hepes (pH 7.4), 1 mM EDTA, 5 mM MgCl$_2$, 1 mM DTT, 0.1% Triton X-100] five times, the bound proteins were eluted with the washing buffer supplemented with 10 mM maltose and resolved by 8% SDS-PAGE according to Laemmli. Laemmli, Nature 227, 680 (1970). The gel was stained with Coomassie brilliant blue R-250, dried, and exposed to X-ray film. The results showed that $^{35}$S-labeled XA21 was only detected in the MBP-XB3 and MBP-XB3ankyrin fractions, and not in the MBP control, confirming that XB3 physically interacts with XA21 and indicating that the ankyrin repeats of XB3 are sufficient for kinase binding.

Example 3

Phosphorylation of XB3 by the XA21 Kinase

The physical interaction between the XA21 kinase and XB3 suggested that XB3 may be a substrate of the XA21 kinase. To test this idea, purified MBP-XB3 protein was incubated with GST-XA21 and [γ-$^{32}$P]ATP in a transphosphorylation assay. GST-XA21 was made using a polynucleotide encoding XA21 that was PCR-amplified with the primers: 5' GGATCCGCACAAGAGAACTAAAAAGG-GAGC 3' (SEQ ID NO:9) and 5' CAGAAGTCGATCT-GAAGTGTGGCA 3' (SEQ ID NO:10) and cloned into the Sma I and Xho I site of GTK carrying GST. See, Stone et al., Plant Physiol. 117, 1217 (1998). 100 ng of purified GST-XA21 was incubated with either 10 ug resin-bound MBP or MBP-XB3 in 20 ul of kinase buffer [50 mM Hepes (pH 7.4), 10 mM MgCl$_2$, 10 mM MnCl$_2$, 1 mM DTT, and 5 uCi (γ-$^{32}$P)ATP (6000 Ci/mmol)] for 90 min at room temperature. The reaction was stopped by adding SDS loading buffer and boiling for 5 min. The proteins were separated by 8% SDS-PAGE, stained, and exposed to X-ray film. The results showed that GST-XA21 phosphorylated itself and MBP-XB3, but not MBP alone.

Example 4

Ubiquitin Ligase Activity of XB3

In animal systems, a number of RING finger-based E3s can catalyze ubiquitination of themselves in an E2 dependent manner. Lorick et al., Proc. Natl. Acad. Sci. U.S.A. 96, 11364 (1999). To determine whether XB3 has this E3 activity, XB3's ability to mediate ubiquitination was examined in an in vitro assay. Various fusion constructs were analyzed including MBP-XB3, MBP-XB3RING (comprising the RING finger domain of native XB3), and MBP-XB3RINGC323A (MBP-XB3RING having the metal-binding residue Cys323 replaced with Ala).

MBP-XB3 was prepared as described in Example 2. The fusion protein MBP-XB3RING was made by PCR-amplifying a polynucleotide encoding the RING finger domain and C-terminal tail of XB3 with the primers: 5' GGATCCATGATATCCGATGCATGCTCAGAG 3' (SEQ ID NO:11) and 5' GGATCCATGATATCGAGGATGAT-GCGGCGA 3' (SEQ ID NO:12), and cloning this polynucleotide into the BamH I site of pMAL-c2X to generate a plasmid designated pMXB3C. pMXB3C was digested with Pst I and self-ligated to remove the portion of the polynucleotide encoding the C-terminal tail of XB3 from the fusion protein. The self-ligated construct was digested with Hind III and self-ligated again to create a stop codon shortly after the nucleotide sequences encoding the RING finger domain. Site-directed mutagenesis was carried out to create of MBP-XB3RINGC323A by following the protocols described in the Quick Change Kit (Stratagene, San Diego, Calif.).

Ubiquitination assays of MBP-XB3, MBP-XB3RING, and MBP-XB3RINGC323A were performed essentially as described in Joazeiro et al., Science 286, 309 (1999); Levkowitz et al., Molecular Cell 4, 1029 (1999); Yoon et al., Science 269, 1102 (1995); and Lorick et al. Proc. Natl. Acad. Sci. U.S.A. 96, 11364 (1999), except for the following modifications: ST-Ub was $^{32}$P-labeled by protein kinase A as described in Scheffner et al., Proc. Natl. Acad. Sci. U.S.A. 91, 8797 (1994). After cleavage with thrombin and depletion with benzamidine Sepharose (Amersham Pharmacia), the labeled Ub ($10^5$ cpm) was incubated with 2 ug MBP-XB3 or other MBP fusion proteins, 2 mM ATP, and 20 ng each of bacterially expressed wheat E1 and UbcH5B in the ubiquitination buffer [50 mM Tris-HCl (pH 7.5), 2.5 mM $MgCl_2$, 0.5 mM DTT] for 90 min at 30° C. The samples were mixed with b-mercaptoethanol-containing loading buffer, separated by 8% SDS-PAGE, stained, and exposed to X-ray film.

The appearance of ubiquitinated XB3 products with high molecular weight was observed only in the presence of UbcH5B. The MBP control was not ubiquitinated. The results also showed that MBP-XB3RING was ubiquitinated, but MBP-XB3RINGC323A was not. Thus, the RING finger domain is necessary for XB3 ubiquitination of itself in an E2-dependent manner.

A ubiquitination assay using $^{32}$P-labeled GST-XA21 was performed to determine if the XA21 kinase is a direct substrate for XB3-mediated ubiquitination. Ubiquitination of XA21 was assessed essentially as described in Joazeiro et al., Science 286, 309 (1999); Levkowitz et al., Molecular Cell 4, 1029 (1999); Yoon et al., Science 269, 1102 (1995), except for the following modifications: 0.5 ug resin-bound GST-XA21 was labeled with [g-$^{32}$P]ATP by autophosphorylation and chased with 1 mM cold ATP for 20 min at room temperature; the resin was then washed once with phosphate-buffered saline containing 0.5 mM EDTA and four times with the ubiquitination buffer [50 mM Tris-HCl (pH 7.5), 2.5 mM $MgCl_2$, 0.5 mM DTT]; the resin-bound GST-XA21 was incubated with 200 ng of wheat E1 and 200 ng UbcH5B, 4 mM ATP, 5 uM cold ubiquitin (Sigma) and 5 ug of MBP-XB3 in the ubiquitination buffer for 90 min at 30° C. The samples were mixed with β-mercaptoethanol-containing loading buffer, separated by 8% SDS-PAGE, stained, and exposed to X-ray film.

The results showed that. ubiquitinated XA21 was only observed when MBP-XB3 was added to the reaction mixture. The RING finger domain of XB3 or MBP alone did not ubiquitinate the XA21 kinase. These results indicated that XA21 is a substrate of the ubiquitin ligase XB3, that the XB3 ankyrin domain is required for recruiting the substrate for ubiquitination, and that the RING finger domain is not sufficient for XA21 ubiquitination.

Example 5

Ubiquitin-Mediated XA21 Degradation

The data from the above examples suggested that ubiquitinated XA21 is targeted for degradation in vivo. To investigate this, transgenic plants carrying a c-myc tagged Xa21 gene (Xa21::myc) were constructed. A c-myc sequence was introduced in the N terminus of the Xa21 gene. The sequence encoding the 13 amino acid c-myc epitope was PCR amplified form the plasmid pATGMyc, verified by sequencing, and cloned into the unique Dra III site of plasmid pC822 to create pC822cMyc. pC822cMyc was then digested with Kpn I and the 9.9 Kb fragment containing the Xa21::myc gene was cloned into the Kpn I site of pCAMBIA 1300. The resulting pC1300-Xa21cMyc construct was transformed into the Agrobacterium strain EHA-105. Agrobacterium-mediated rice transformation was carried out as described below.

Seeds were dehusked and sterilized in 70% ethanol for one minute and then in 20% sodium hypochlorite for 1 h, washed several times with sterile water, and cultured on callus induction medium (MS basal medium supplemented with 2.0 mg/l 2,4-D, 500 mg/l casamino acids, 500 mg/l proline, 30 g/l sucrose, and 2.5 g/l phytagel, pH 5.8). Four-week-old calli were used for transformation. They were removed from seeds and divided into small pieces (1–2 mm in diameter) and subcultured for 4–5 days on callus induction medium. Infection of calli was carried out using Agrobacterium tumefaciens strain EHA 105 containing pCAMBIA1301-based constructs that contain genes for hygromycin resistance and GUS. EHA 105 was grown for two days at 28° C. on AB medium supplemented with 50 mg/l hygromycin and 50 mg/l kanamycin. The bacteria were collected, resuspended in AAM medium supplemented with acetosyringone (100 uM), and allowed to grow for 1 h at 28° C. The calli were immersed in the bacterial suspension, swirled, and incubated for 30 min. They were then transferred to MS-AS medium (MS basal, 500 mg/l casamino acids, 500 mg/l proline, 2 mg/l 2,4-D, 30 g/l sucrose, 10 g/l glucose, 100 uM acetosyringone, 2.5 g/l phytagel, pH 5.2) and co-cultivated for 3 days in the dark at 26° C. The calli were washed with 250 mg/l carbenecillin, incubated on MS-CH selection medium (callus induction medium with 50 mg/l hygromycin and 250 mg/l carbenecillin, pH 5.8) in the dark at 26° C., and transferred to new plates every two weeks. Resistant calli which appeared after 4–6 weeks were transferred to regeneration medium (MS basal, 2.0 mg/l kinetin, 30 g/l sucrose, 50 mg/l hygromycin, 250 mg/l carbenecillin, 4.0 g/l phytagel, pH 5.8) and incubated under 16 h light/8 h dark cycle. Plants regenerated within 4 weeks. The putative transgenics were moved to magenta boxes for shoot elongation (MS basal, 30 g/l sucrose, 2.5 g/l phytagel, pH 5.8). After two weeks, the plants were transplanted into pots and grown in the greenhouse. DNA and RNA gel blot analyses, GUS assays (Jefferson et al., EMBO J 6: (1987)), and PCR were performed to determine presence and expression of the transgene. See, L. L. Ilag, R. C. Yadav, N. Huang, P. C. Ronald, and F. M. Ausubel, Gene 255:245, 2000.

Transgenic rice plants carrying Xa21::myc were inoculated with race 6 of Xoo. A typical resistant phenotype was observed in the transgenic plants, indicating that Xa21::myc functions in this respect as the wildtype Xa21 gene. A Western blot probed with anti-MYC antibodies was performed. In this blot, a 164 kD band was detected in the resistant transgenic plants, but not in the recipient line Taipei309. Two additional products with the size of 180 and 140 kD were found in both transgenic and nontransgenic plants. A cosegregation analysis (for Myc expression and resistance) indicated that the 164 kD band was XA21::MYC (i.e., the protein produced by Xa21::myc), and that the 180 and 140 kD products were unrelated to XA21 and could therefore serve as internal controls in a Western blot analysis.

To examine whether XA21 is degraded upon pathogen inoculation, the endogenous XA21 was monitored with anti c-MYC antibodies in the total protein extract isolated from the transgenic Xa21::cmyc plants. Six-week-old transgenic plants carrying Xa21::myc were inoculated with Xoo race 6 strain PXO99Az using the leaf-clip method. Kauffman, et al., Plant Dis. Rep. 57, 537 (1973). 0.5 cm of leaf tip tissue was harvested at 0, 6, 12 hours after inoculation and total proteins were isolated from the leaves. Protein extracts (50 ug) were separated in a 6% SDS-PAGE. After electrophoresis, the gel was electroblotted to a PVDF membrane (Millipore) for one hour at 100 v. The non-specific binding sites on the membrane were then blocked with Blotto (5% non-fat dried milk in 0.1% tween; 100 mM Tris-HCl pH 7.9; 150 mM NaCl [TTBS]) for 60 min at room temperature. Incubation with the anti c-MYC monoclonal antibody (1 ug/ml) (obtained from Calbiochem, CA) was performed in 3% bovine serum albumin in TTBS for two hours at room temperature followed by three 10 minute washes in TTBS. Then the membrane was incubated with the secondary antibody (goat anti mouse-IgG-HRP Sigma) at a one in 5000 dilution in 5% non-fat dried milk/TTBS for one hour at room temperature, followed by three 10 minute washes in TTBS. The blot was developed with the ECL+ Plus kit from Amersham (Amersham Pharmacia Biotech Inc., Piscataway, N.J.).

The results showed that XA21 expression was dramatically decreased six hours after inoculation with the avirulent Xoo Philippine race 6. In contrast, only a slight decline of XA21 was observed over the time period in the transgenic plants when challenged with the virulent Xoo Korean race 1. These results support the hypothesis that upon recognition of a pathogen-produced effector protein, the activated XA21 is targeted for degradation by the ubiquitin ligase XB3.

Example 6

Inhibition of XB3 Expression

Various methods form modulating plant resistance to disease by modulating expression of XB3 are within the invention. Any technique known to alter expression of a gene or functional activity of a gene product in plants can be used in the invention including. Such techniques include e.g., expressing antisense nucleic acids that hybridize to mRNAs encoding XB3, using RNA interference (see, e.g., C. Chaung and E. M. Meyerowitz, Proc. Nat'l. Acad. Sci. USA, 97:4985 (2000)), expressing truncated variants of XB3 (e.g., the ankyrin domain of native XB3) or mutated variants of XB3 (e.g., those lacking the conserved Cys or His essential for ubiquitination activity) that bind to XA21 but do not target XA21 for degradation, and expressing genes producing antibodies within a plant cell that bind endogenous XB3. Using other methods, plant expression of an endogenous XB3 can be knocked out using T-DNA or chemical-mediated mutagenesis. Mutants displaying stable and broad spectrum resistance can be selected using conventional methods. Additionally, using the nucleotide sequence of Xb3 or amino acid sequence of native XB3, other genes related to Xb3 from various other rice species or non-rice plants can be cloned and manipulated, e.g., to develop increased disease resistance in such other species or plants. For instance, using the sequences disclosed herein to search Genbank, rice ESTs (Accession Nos. AU030853, AU062419, C91740, D15769, D24524, D39809) and a tomato ortholog (Accession No. AW031308) were identified.

Example 7

Transgenic Plants

The invention provides various transgenic plants. A transgenic plant can be made by transforming a plant cell with an antisense Xb3 oligonucleotide, a nucleotide expressing a dominant-negative Xb3 mutant, or RNAi construct. Oligonucleotides transformed into a cell of a rice plant having or lacking functional Xa21 can be driven by ubiquitin, a 35S promoter, or an inducible promoter (especially in the case where constitutive reduction of XB3 expression causes a lethal phenotype). An established inducible system suitable for use with rice has been described by (Aoyama and Chua, Plant J, 11:605, 1997).

Example 8

XB3 Functions as a Negative Regulator Preventing the Accumulation of XA21

Construction of Rice Transformation Plasmids:

The RNAi construct RNAiXb3 was made according to Chuang and Meyerowitz (Proc. Nat'l Acad. Sci. USA 97: 4985 (2000)) with some modifications. The 3' end of Xb3 containing nucleotides 1113–1414 was PCR amplified with the following primers: XB3-14 (5' GAATTCTCTAGAC-CGGGGCAGCATCTCA 3' (SEQ ID NO:13)), XB3-15 (5' ACTAGTGGATCCTTTCTGATACCAACGGA 3' (SEQ ID NO:14)), XB3-16 (5' GAATTCAGATCTCCGGGGCAG-CATCTCA 3' (SEQ ID NO:15)), XB3-17 (5' ACTAGT-GATATCTTTCTGATACCAACGGA 3' (SEQ ID NO:16)). The PCR products were cloned, sequenced to confirm that no PCR error was introduced, and ligated to the β-glucuronidase fragment spanning nucleotides 815–1793 in both antisense and sense orientations. The resulting construct was inserted into the overexpression vector pBHU-1, containing the hph gene whose product confers resistance to hygromycin B, between the maize ubiquitin promoter and the nos 3' terminator.

To generate dominant-negative mutants, the Xb3 sequence encoding the ankyrin domain (nucleotides 1–976) was PCR amplified with the primers: XB3-1 (5' GGATC-CATGATATCCATGGGTCACGGTGTC 3' (SEQ ID NO:7)) and XB3-6 (5' CGGGATCCGATATCAGATGCAG-CAAAGCTCC 3' (SEQ ID NO:8)). The PCR product was cloned, verified by DNA sequencing, and inserted into pBHU-1 between the maize ubiquitin promoter and the nos 3' terminator. The resulting construct was designated pBHUXb3ank.

Plant Transformation and Inoculation:

Transgenic plants were generated according to Jiang et al. (Crop Science 40: 1729, 2000). After regeneration, small shoots were transferred to Magenta boxes containing a medium with half-strength MS basal salts, 0.1% (w/v) sucrose, 0.25% (w/v) Phytagel, and 25 ug/ml hygromycin B. Spontaneous lesions were scored at this stage. Plants were then transplanted into soil and maintained in greenhouse. Inoculation of transgenic plants with Xoo race 6 strain PXO99Az was carried out according to Kauffman et al. (Plant Dis Rep 57: 537). The strain was grown for 3 days at 30° C. on the PSA medium containing 1% (w/v) peptone, 1% (w/v) sucrose, and 0.1% (w/v) sodium glutamate. The bacterial cells were resuspended into water to make a final concentration of $10^9$ cells/ml. Six-week-old plants were cut ~4 cm below the tips with scissors dipped in the bacterial suspension prepared above. After inoculation, the plants were maintained in a growth chamber. Lesion development was scored 11 days after inoculation.

Trypan Blue Staining:

Trypan blue staining was carried out according to Bowling et al. (Plant Cell 9: 1573). Leaves with lesions were submerged in LPTB solution (2.5 mg/ml Trypan blue, 25% [w/v] lactic acid, 23% water-saturated phenol, 25% glycerol and water), infiltrated for 10 min, heated over boiling water for 2 min, and stained overnight. Destain was performed in LPB (LPTB without trypan blue) solution with multiple changes for 4 days. Samples were finally equilibrated with 70% glycerol for microscopy analysis.

PCR Analysis of Transgenic Plants:

To confirm the presence of the c-myc tagged Xa21 gene, genomic DNA was isolated from the transgenic plants using the method described by Williams and Ronald (Nucleic Acids Res. 22: 1917). The region containing the insertion site of the c-myc tag was PCR amplified using the primers: ALF-8 (5' GAATTCGCGCTGCTCTC 3' (SEQ ID NO:17)) and ALF-9 (5' GGTGCATGCTCCAATGG 3' (SEQ ID NO:18)), and the following conditions: 5 cycles with denaturing at 94° C. for 1 min, annealing at 45° C. for 1 min, and extension at 72° C. for 1 min; followed by 30 cycles with denaturing at 94° C. for 1 min, annealing at 60° C. for 1 min, and extension at 72° C. for 1 min. The PCR products were resolved by 5% PAGE gel.

RNA Isolation and Quantitation:

Total RNA was isolated from 100 mg of rice leaf tissue with the use of the RNeasy Plant Mini Kit (Qiagen) and treated with DNase I (RNase-free) to degrade contaminating genomic DNA. To determine the levels of the endogenous Xb3 mRNA, TaqMan PCR was carried out using the GeneAmp ABI5700 Sequence Detection System in combination with the primers TaqmanXB3-1 (5' GCGCTGAAACGGAACCATGGA 3' (SEQ ID NO:19)) and TaqmanXB3-2 (5' GCTTCTGGTTCAAGCTCACTGA 3' (SEQ ID NO:20)), the probe TaqmanXB3-3 (5'TGTGCAGCTTTGCTGAACCCTACATCA 3' (SEQ ID NO:21) conjugated with 6FAM (6-carboxyflurescein) on its 5' end and with TAMRA (6-carboxy-N,N,N',N'-tetramethylrhodamine) on its 3' end), and the TaqMan One-Step RT-PC Master Mix Reagents kit (Perkin-Elmer) according to the manufacturer's instructions. For rRNA quantitation, the TaqMan Ribosomal Control Reagent kit (Perkin-Elmer) was used according to manufacturer's instructions. Data were analyzed using Sequence Detector software (Perkin-Elmer) setting the baseline and threshold manually for each experiment. The threshold for Xb3 was 0.025 and for 18 s rRNA was 0.05.

Results:

The biological role of Xb3 in vivo was examined using two approaches: RNAi and overexpressing the ankyrin domain of Xb3 to create dominant-negative mutants. The RNAiXb3 construct was co-transformed with Xa21::myc into the susceptible rice cultivar Taipei309 (TP309) using particle bombardment. Transgenic plants were regenerated from calli showing resistance to hygromycin B. On average, 2–3 plants were subsequently propagated from each transgenic line. Interestingly, twenty-nine of fifty-one independent transgenic lines showed development of spontaneous necrotic lesions even when these plants were maintained in sterile conditions. PCR analysis demonstrated that at least one of the twenty-nine lines showing spontaneous lesions does not carry Xa21::myc. Thus, the formation of spontaneous lesions is independent of the presence of Xa21::myc. To determine whether the spontaneous lesion formation is associated with cell death, leaves with visible lesions were stained with trypan blue, a histochemical indicator of cell death. Several areas of the leaf with lesions are stained dark blue indicating that cell death occurs.

To demonstrate that the lesion mimic phenotype observed is due to a reduction in Xb3 levels, five independent transgenic lines showing severe spontaneous lesions were chosen to quantify the levels of the endogenous Xb3 mRNA using TaqMan PCR assays. The TaqMan primers and probe were designed according to the Xb3 sequence that was not included in the RNAiXb3 construct, therefore the PCR system specifically detects the endogenous Xb3 mRNA rather than the RNA produced by the RNAiXb3 transgene. The resulting data showed that the endogenous levels of Xb3 were significantly reduced in the lesion mimic lines to as low as 9.8% when compared with those in 4021-3 plants which were only transformed with Xa21::myc. These results show that the decrease of Xb3 mRNA is responsible for the lesion development. Taken together, our data indicate that Xb3 functions as a cell death suppressor.

The dominant-negative mutants were generated by co-transforming TP309 with Xa21::myc and pBHUXb3ank. Fourteen of twenty five transgenic plants showed development of spontaneous lesions similar to those observed in the RNAiXb3 plants described above. This result confirms that the lesion mimic phenotype is the result of alteration in XB3 and indicates that the ankyrin repeats of XB3 function as a recognition domain for substrate.

To test the hypothesis that XB3 is also a negative regulator of XA21, a total of 135 plants, representing 51 independent lines co-transformed with RNAiXb3 and Xa21::myc were inoculated with Xoo race 6, a race that is avirulent to Xa21. Only eight plants, arising from three independent transgenic lines showed a significant reduction in lesion length as compared with susceptible controls. PCR analysis demonstrated that all of the resistant lines contain Xa21::myc. These results indicate that the transgenic resistant lines carry at least one functional copy of Xa21::myc. Compared with the results from previous transformation experiments (9 of 15 lines are resistant; Song et al., Science 270: 1804 (1995)), the efficiency of co-expression of two transgenes (3 of 51 lines) is significantly lower in the Xa21::myc/RNAiXb3 experiments. Interestingly, Western blot analysis using anti-c-MYC antibody did not detect XA21::MYC in total protein extracts from the transgenic lines showing resistance to Xoo race 6. In contrast, XA21::MYC could be easily detected in the resistant lines (e.g., 4021-3) that were only transformed with Xa21::myc. To demonstrate equal loading, a duplicate blot was probed with the antibodies specific to the plasma membrane-localized ATPase. No significant difference was observed from all the lines tested. Thus, the three resistant lines must carry dramatically decreased levels of XA21::MYC rather than absence of the resistance protein. TaqMan PCR analysis indicated that the mRNA levels of Xb3 are reduced in these three resistant lines compared with those in 4021-3. The strict correlation between the low levels of XA21 and the reduced Xb3 mRNA strongly suggests that the XB3 protein plays an important role in regulation of XA21. Activation of the XA21 kinase in rice can cause cell death (He et al., Science 288: 2360). Thus the high levels of XA21 in plants with decreased Xb3 could cause lethality during the tissue culture process.

Other Embodiments

This description has been by way of example of how the compositions and methods of invention can be made and carried out. Various details may be modified in arriving at the other detailed embodiments, and many of these embodiments will come within the scope of the invention. Therefore, to apprise the public of the scope of the invention and the embodiments covered by the invention, the following claims are made.

What is claimed is:

1. A purified nucleic acid comprising SEQ ID NO:1 that encodes XB3 protein.
2. A purified nucleic acid encoding a protein having the amino acid sequence of SEQ ID NO:2.
3. A vector comprising the nucleic acid of claim 1 or 2.
4. The vector of claim 3, wherein said nucleic acid is operably linked to one or more expression control sequence.
5. A transformed host cell comprising the purified nucleic acid of claim 1 or 2.
6. A method of transforming a plant cell or seed, the method comprising the steps of:
   (a) providing a plant cell or seed; and
   (b) introducing into the plant cell or seed a purified nucleic acid that encodes the amino acid sequence of SEQ ID NO:2.
7. The method of claim 6, wherein the purified nucleic acid has the nucleotide sequence of SEQ ID NO:1.

* * * * *

SEQUENCE LISTING

<160> NUMBER OF SEQ ID NOS: 24

<210> SEQ ID NO 1
<211> LENGTH: 1353
<212> TYPE: DNA
<213> ORGANISM: Oryza sativa

<400> SEQUENCE: 1

```
atgggtcacg gtgtcagctg cgcccgcacc ggcgacgagc acgacttctt ccgggcggcg      60
cagctcggcg acctcgacgc cctggccgcc ctcctcgccg ccgacccttc cctcgctcgc     120
cgcgccaccc tctacgaccg cctctccgtc ctccacatcg ccgccgccaa tggccgcatc     180
gaggtgctct ccatgttctt ggatcgcggg gcgccgccgg acgcggtgaa tcggcacaag     240
cagacgccgc tgatgctcgc ggccatgcac ggcaagatcg actgcgtgct caagctcctc     300
caggccgacg caaatatctt gatgttcgac tcggtgcacg cgaggacctg cctccaccac     360
gcggcgtact acggccacgt cgactgcctg caggccatcc tcgccgccgc gcagaccacg     420
ccggtggccg actcatgggg tttcgcccgg ttcgtcaacg tcagggacga ccacggcgcc     480
actccgctgc atctcgcggc caggcagggg cggccggggt gcgtgcaggt gttgctggag     540
aacggcgcca ttgtgtcggc tttgacagga tcatatggct tccctggaag cacgtcgctt     600
catttggctg ctcgtagcgg gaacttggat tgcatcagga agctgcttgc ctggggagct     660
gatcggctcc aaagggattc ggctgggaga attccctatt ctgttgcgct gaaacggaac     720
catggagcat gtgcagcttt gctgaaccct acatcagcag agcccatggt gtggccatcc     780
ccacttaagt tcatcagtga gcttgaacca gaagctaagg ctctcctgga agcagctctg     840
atggaagcca acagggagag ggagaagaaa atcctgaatg cacaaagta ctccctgcca     900
tccccttcgc ccggtgatga cagtgccgat gacgatgcat gctcagaggt gagcgacacg     960
gagctttgct gcatctgctt cgaccaggct tgcaccattg aggtgcaaga ctgtggacat    1020
caaatgtgtg caccgtgcac gctggcactg tgctgtcaca acaaacccaa tccgacgacc    1080
ctgacaccgc cctcaccggc ctgcccattc tgccggggca gcatctcacg gctggtggtg    1140
gcccaaacaa ggtctgcttg tgatcctgac aagccgtcat ccctgcagct cacccggaag    1200
cggtcgcgtc gatctcacaa cctcagtgag ggcagcagca gcttcaaagg gctaccttcg    1260
gccatgggct ccttctcaaa gcttggccgt ggctcgagcc gcatggcgga cagtgacagc    1320
agcaacctgg acaagcctga gcacgatcta tga                               1353
```

<210> SEQ ID NO 2
<211> LENGTH: 450
<212> TYPE: PRT
<213> ORGANISM: Oryza sativa
<220> FEATURE:
<221> NAME/KEY: MOD_RES
<222> LOCATION: (258)
<223> OTHER INFORMATION: Any amino acid

<400> SEQUENCE: 2

```
Met Gly His Gly Val Ser Cys Ala Arg Thr Gly Asp Glu His Asp Phe
 1               5                  10                  15

Phe Arg Ala Ala His Leu Gly Asp Leu Asp Ala Leu Ala Ala Leu Leu
                20                  25                  30

Ala Ala Asp Pro Ser Leu Ala Arg Arg Ala Thr Leu Tyr Asp Arg Leu
            35                  40                  45

Ser Val Leu His Ile Ala Ala Asn Gly Arg Ile Glu Val Leu Ser
     50                  55                  60

Met Phe Leu Asp Arg Gly Ala Pro Pro Asp Ala Val Asn Arg His Lys
 65                  70                  75                  80

Gln Thr Pro Leu Met Leu Ala Ala Met His Gly Lys Ile Asp Cys Val
                 85                  90                  95

Leu Lys Leu Leu Gln Ala Asp Ala Asn Ile Leu Met Phe Asp Ser Val
            100                 105                 110

His Ala Arg Thr Cys Leu His His Ala Ala Tyr Tyr Gly His Val Asp
        115                 120                 125

Cys Leu Gln Ala Ile Leu Ala Ala Gln Thr Thr Pro Val Ala Asp
130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asn
        195                 200                 205

Leu Asp Cys Ile Arg Lys Leu Leu Ala Trp Gly Ala Asp Arg Leu Gln
210                 215                 220

Arg Asp Ser Ala Gly Arg Ile Pro Tyr Ser Val Ala Leu Lys Arg Asn
225                 230                 235                 240

His Gly Ala Cys Ala Ala Leu Leu Asn Pro Thr Ser Ala Glu Pro Met
                245                 250                 255

Val Xaa Pro Ser Pro Leu Lys Phe Ile Ser Glu Leu Glu Pro Glu Ala
            260                 265                 270

Lys Ala Leu Leu Glu Ala Ala Leu Met Glu Ala Asn Arg Glu Arg Glu
        275                 280                 285

Lys Lys Ile Leu Asn Gly Thr Lys Tyr Ser Leu Pro Ser Pro Ser Pro
            290                 295                 300

Gly Asp Asp Ser Ala Asp Asp Ala Cys Ser Glu Val Ser Asp Thr
305                 310                 315                 320

Glu Leu Cys Cys Ile Cys Phe Asp Gln Ala Cys Thr Ile Glu Val Gln
                325                 330                 335

Asp Cys Gly His Gln Met Cys Ala Pro Cys Thr Leu Ala Leu Cys Cys
            340                 345                 350

His Asn Lys Pro Asn Pro Thr Thr Leu Thr Pro Pro Ser Pro Ala Cys
        355                 360                 365

Pro Phe Cys Arg Gly Ser Ile Ser Arg Leu Val Val Ala Gln Thr Arg
    370                 375                 380

Ser Ala Cys Asp Pro Asp Lys Pro Ser Ser Leu Gln Leu Thr Arg Lys
385                 390                 395                 400
```

```
Arg Ser Arg Arg Ser His Asn Leu Ser Glu Gly Ser Ser Ser Phe Lys
            405                 410                 415

Gly Leu Pro Ser Ala Met Gly Ser Phe Ser Lys Leu Gly Arg Gly Ser
            420                 425                 430

Ser Arg Met Ala Asp Ser Asp Ser Ser Asn Leu Asp Lys Pro Glu His
            435                 440                 445

Asp Leu
    450

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
gtcgaccaga tctcataaga gaagaaaga                                     29

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 4
gtcgacgaat gaaatcagtt gtgaagggta c                                  31

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 5
ggatccgtcg accacaagag aactaaaaag ggagc                              35

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 6
ggatccgtcg accccgggca gaagtcgatc tgaagtgtgg ca                      42

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 7
ggatccatga tatccatggg tcacggtgtc                                    30

<210> SEQ ID NO 8
<211> LENGTH: 31
<212> TYPE: DNA
<213> ORGANISM: Artificial Sequence
<220> FEATURE:
```

<223> OTHER INFORMATION: Description of Artificial Sequence: Primer

<400> SEQUENCE: 8
cgggatccga tatcgatgc agcaaagctc c                     31

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
ggatccgcac aagagaacta aaaagggagc                      30

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
cagaagtcga tctgaagtgt ggca                            24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
ggatccatga tatccgatgc atgctcagag                      30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
ggatccatga tatcgaggat gatgcggcga                      30

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 13
gaattctcta gaccggggca gcatctca                        28

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 14
actagtggat cctttctgat accaacgga                       29

```
<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 15
gaattcagat ctccggggca gcatctca                                       28

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 16
actagtgata tctttctgat accaacgga                                      29

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 17
gaattcgcgc tgctctc                                                   17

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 18
ggtgcatgct ccaatgg                                                   17

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 19
gcgctgaaac ggaaccatgg a                                              21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 20
gcttctggtt caagctcact ga                                             22

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Primer
```

```
<400> SEQUENCE: 21
tgtgcagctt tgctgaaccc tacatca                                    27

<210> SEQ ID NO 22
<211> LENGTH: 50
<212> TYPE: PRT
<213> ORGANISM: Oryza sativa

<400> SEQUENCE: 22

Cys Cys Ile Cys Phe Asp Gln Ala Cys Thr Ile Glu Val Gln Asp Cys
 1               5                  10                  15

Gly His Gln Met Cys Ala Pro Cys Thr Leu Ala Leu Cys Cys His Asn
            20                  25                  30

Lys Pro Asn Pro Thr Thr Leu Thr Pro Pro Ser Pro Ala Cys Pro Phe
        35                  40                  45

Cys Arg
    50

<210> SEQ ID NO 23
<211> LENGTH: 40
<212> TYPE: PRT
<213> ORGANISM: Homo sapiens

<400> SEQUENCE: 23

Cys Lys Ile Cys Ala Glu Asn Asp Lys Asp Val Lys Ile Glu Pro Cys
 1               5                  10                  15

Gly His Leu Met Cys Thr Ser Cys Leu Thr Ser Trp Gln Glu Ser Glu
            20                  25                  30

Gly Gln Gly Cys Pro Phe Cys Arg
        35                  40

<210> SEQ ID NO 24
<211> LENGTH: 36
<212> TYPE: PRT
<213> ORGANISM: Unknown Organism
<220> FEATURE:
<223> OTHER INFORMATION: Description of Unknown Organism: Baculovirus
      inhibitor of apoptosis

<400> SEQUENCE: 24

Cys Lys Ile Cys Tyr Val Glu Glu Cys Ile Val Cys Phe Val Pro Cys
 1               5                  10                  15

Gly His Val Val Ala Cys Ala Lys Cys Ala Leu Ser Val Asp Lys Cys
            20                  25                  30

Pro Met Cys Arg
        35
```